United States Patent [19]

Kalopissis

[11] 4,394,520
[45] Jul. 19, 1983

[54] 5-UREIDO-3-THIA HEXANEDIOIC ACID

[75] Inventor: Gregoire Kalopissis, Paris, France

[73] Assignee: Societe Anonyme dite: L'Oreal, Paris, France

[21] Appl. No.: 108,829

[22] Filed: Dec. 31, 1979

Related U.S. Application Data

[60] Division of Ser. No. 871,839, Jan. 24, 1978, Pat. No. 4,204,064, which is a division of Ser. No. 714,004, Aug. 12, 1976, Pat. No. 4,085,217, which is a division of Ser. No. 501,615, Aug. 29, 1974, Pat. No. 3,976,781, which is a division of Ser. No. 203,046, Nov. 29, 1971, Pat. No. 3,849,576, which is a continuation-in-part of Ser. No. 736,960, Jun. 14, 1968, abandoned, which is a continuation-in-part of Ser. No. 427,976, Jan. 25, 1965, abandoned, and Ser. No. 602,480, Dec. 19, 1966, abandoned, Ser. No. 794,363, Jan. 27, 1969, abandoned, Ser. No. 801,840, Feb. 24, 1969, abandoned, Ser. No. 817,193, Apr. 17, 1969, abandoned, Ser. No. 858,161, Sep. 15, 1969, Pat. No. 3,671,643, Ser. No. 12,122, Feb. 17, 1970, abandoned, and Ser. No. 36,405, May 11, 1970, abandoned.

[30] Foreign Application Priority Data

| Jan. 29, 1964 | [FR] | France | 64 961897 |
| Dec. 22, 1965 | [LU] | Luxembourg | 50125 |
| Jun. 21, 1967 | [FR] | France | 67 111396 |
| Jul. 28, 1967 | [FR] | France | 67 116160 |
| Jan. 29, 1968 | [LU] | Luxembourg | 55371 |
| Feb. 23, 1968 | [LU] | Luxembourg | 55553 |
| Feb. 19, 1969 | [LU] | Luxembourg | 58042 |
| Apr. 19, 1969 | [LU] | Luxembourg | 55935 |
| Jun. 3, 1969 | [BE] | Belgium | 74877 |
| May 12, 1969 | [LU] | Luxembourg | 58634 |
| Apr. 23, 1971 | [LU] | Luxembourg | 63056 |
| Apr. 23, 1971 | [LU] | Luxembourg | 63057 |

[51] Int. Cl.$^3$ .................................. C07C 149/437
[52] U.S. Cl. .................................................. 562/557
[58] Field of Search .................. 560/16, 153; 562/426, 562/556, 557; 260/402.5, 390

[56] References Cited

U.S. PATENT DOCUMENTS

| 2,431,967 | 12/1947 | Safir | 560/16 |
| 2,466,232 | 4/1949 | Harris | 560/16 |
| 2,537,892 | 1/1951 | Harris | 560/16 |
| 2,539,854 | 1/1951 | Mozingo | 562/557 |
| 2,723,972 | 11/1955 | Herrick | 560/16 |
| 2,955,036 | 10/1960 | Dersch | 430/401 |
| 3,624,143 | 11/1971 | Shen | 560/16 |

FOREIGN PATENT DOCUMENTS 585581 2/1947 United Kingdom ................ 562/557

OTHER PUBLICATIONS

Greenstein, "Chemistry of the Amino Acids," vol. 3, pp. 1894–1897, 1920–1922 & 2646–2650 (1961).

Primary Examiner—Michael L. Shippen
Attorney, Agent, or Firm—Cushman, Darby & Cushman

[57] ABSTRACT

A method, composition and compounds useful in said compositions for treating the skin and scalp characterized by an excessive secretion of sebum to improve the condition thereof by reducing said excessive secretion of sebum includes topically applying to a human having skin and/or a scalp so characterized a cosmetic composition containing as an active ingredient a derivative of cysteine or cysteamine. The composition contains about 0.1–5 weight percent of said derivative and also contains as a carrier for the active ingredient, water, a mixture of water and a lower alkanol, a lower alkanol, a mixture of a lower alkanol and a cosmetic resin, a reducing agent, a neutralizing agent or a vegetable oil.

1 Claim, No Drawings

5-UREIDO-3-THIA HEXANEDIOIC ACID

This application is a division of application Ser. No. 871,839, filed Jan. 24, 1978, now U.S. Pat. No. 4,204,064, which is a division of application Ser. No. 714,004, filed Aug. 12, 1976, now U.S. Pat. No. 4,085,217 which is a division of application Ser. No. 501,615, filed Aug. 29, 1974, now U.S. Pat. No. 3,976,781, which is a division of application Ser. No. 203,046, filed Nov. 29, 1971, now U.S. Pat. No. 3,849,576, which is a continuation-in-part of copending earlier filed applications Ser. No. 736,960 filed June 14, 1968, now abandoned, which in turn is a continuation-in-part of applications Ser. No. 427,976, filed Jan. 25, 1965, now abandoned, and Ser. No. 602,480, filed Dec. 19, 1966, now abandoned, Ser. No. 794,363, filed Jan. 27, 1969, now abandoned, Ser. No. 801,840, filed Feb. 24, 1969, now abandoned, Ser. No. 817,193, filed Apr. 17, 1969, now abandoned, Ser. No. 858,161, filed Sept. 15, 1969, now U.S. Pat. No. 3,671,643, Ser. No. 12,122, filed Feb. 17, 1970, now abandoned, and Ser. No. 36,405, filed May 11, 1970, now abandoned, all of which are incorporated herein by reference.

The present invention relates to a composition and method for treating skin and scalp characterized by an excessive secretion of sebum, to improve the condition thereof by reducing said excessive secretion comprising topically applying to a human being having skin and/or a scalp so characterized an effective amount of a composition comprising a non-toxic cosmetic carrier suitable for topical application to the scalp or skin and as a non-toxic active compound, certain thioethers which are cysteine or cysteamine derivatives.

The active compound employed in the present invention is selected from the group consisting of a compound having the formula

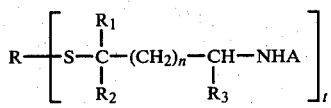
(I)

and the acid salts thereof, wherein n is 0 or 1 and when n is 0, $R_1$ and $R_2$ are selected from the group consisting of hydrogen and $CH_3$ and when n is 1, $R_1$ and $R_2$ are hydrogen;

$R_3$ is selected from the group consisting of hydrogen and $-COR_7$ wherein $R_7$ is selected from the group consisting of hydroxy, alkoxy containing 1–5 carbon atoms, glucosamine, $-NH-NH_2$, $-NHOH$,

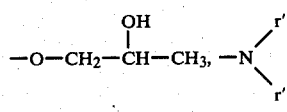

wherein r' represents a member selected from the group consisting of hydrogen and alkyl having 1–3 carbon atoms,

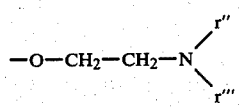

wherein r'' and r''' each independently represent alkyl having 1–3 carbon atoms or together with the nitrogen atom to which they are attached form a ring selected from the group consisting of morpholine, piperidine, pyrrolidine and N'-methylpiperazine;

A is selected from the group consisting of hydrogen, $-CONH_2$,

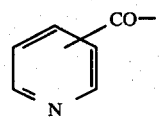, glutamyl, $-COR_4$ and $-SO_2R_6$ wherein $R_4$ is selected from the group consisting of hydrogen, alkyl having 1–18 carbon atoms, alkenyl having 2–18 carbon atoms,

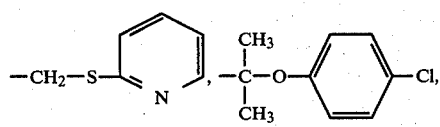

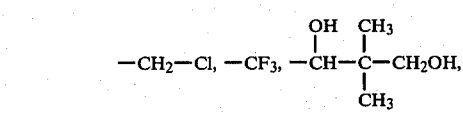

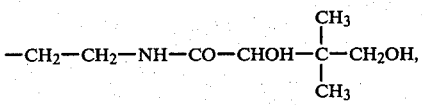

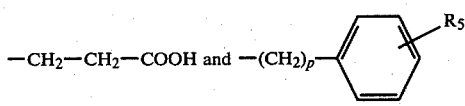

wherein p is 0–1 and $R_5$ is selected from the group consisting of hydrogen, alkyl having 1–4 carbon atoms, alkoxy having 1–4 carbon atoms, halogen and acetamide, and wherein $R_6$ is selected from the group consisting of alkyl having 1–4 carbon atoms,

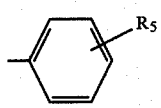

wherein $R_5$ has the meaning given above and $-CH_2-CO-C_6H_5$, t is 1 or 2 and when t is 1, R is selected from the group consisting of linear or branched chain alkyl having 1–18 carbon atoms when $R_3$ is hydrogen or $COR_7$ and n is 0, linear or branched chain alkenyl having 3–18 carbon atoms, propyne-2 yl, mono- or dihydroxyalkyl containing 2–4 carbon atoms, 1,2-dichlorovinyl,
$-C(C_6H_5)_3$, $-C(CH_3)_3$, $-CH(C_6H_5)_2$, $-CH(C_6H_4 \text{ p}-OCH_3)_2$, $-C(CH_3)_2(C_6H_4 \text{ p}-OCH_3)$, $-CONH_2$,

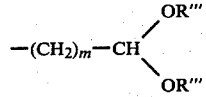

wherein R''' is alkyl having 1–4 carbon atoms and m is 1–2,

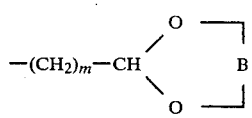

wherein m is 1-2 and B is selected from the group consisting of

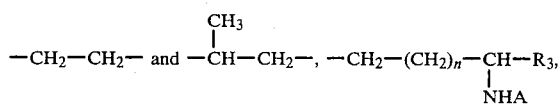

wherein n, $R_3$ and A have the meanings given above, $-(CH_2)_s-COR_{10}$ wherein s is 1-5 and $R_{10}$ is selected from the group consisting of $R_7$, piperidino, morpholino, pyrrolidino, N'-methylpiperazino and $-N(CH_2-CH_2OH)_2$, $-(CH_2)_z-R_8$ wherein z is 0, 1 or 2 and when z is 0, $R_8$ is selected from the group consisting of naphthyl-1, naphthyl-2, pyridyl-2, pyridyl-2 substituted with a member selected from the group consisting of nitro and alkyl having 1-4 carbon atoms, and pyridyl-2-N oxide when $R_3$ is hydrogen, and when z is 1, $R_8$ is selected from the group consisting of naphthyl-2, naphthyl-2, thienyl-2, tetrahydrofuryl-2, furyl-2, pyridyl-2, pyridyl-2 substituted with a member selected from the group consisting of nitro and alkyl having 1-4 carbon atoms, and pyridyl-2-N-oxide and when z is 2, $R_8$ is selected from the group consisting of pyridyl-2, pyridyl-2 substituted with a member selected from the group consisting of nitro and alkyl having 1-4 carbon atoms and pyridyl-2-N-oxide, and

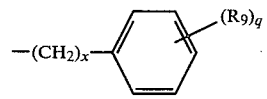

wherein x is 0-2 and wherein when q is 1, 2 or 3, $R_9$ is selected from the group consisting of hydrogen, halogen, alkoxy having 1-5 carbon atoms and linear or branched chain alkyl having 1-4 carbon atoms, and when q is 1, $R_9$ is selected from the group consisting of acetamido, amino, phenoxy, cyclohexyl, methylenedioxy, trifluoromethyl, nitro, phenyl, dialkylamino wherein each alkyl moiety has 1-5 carbon atoms, alkylthio having 1-5 carbon atoms, alkylsulfinyl having 1-5 carbon atoms and alkylsulfonyl having 1-5 carbon atoms, and when t is 2, R is selected from the group consisting of alkylene having 2-4 carbon atoms, alkylene having 2-4 carbon atoms and substituted with 1-2 hydroxy groups, butenylene and $-(CH_2)_2-SO_2-(CH_2)_2-$.

When the above active compounds contain at least one primary amine group, they can be used as salt with an inorganic or organic acid selected from the group consisting of hydrochloric, hydrobromic, sulfuric, phosphoric, p-toluene sulfonic, dihydrocinnamic, cinnamic, mandelic, salicylic, tropic, oxalic, malic, tartaric, succinic, acetic, lactic, 3-hydroxy butyric, fumaric, undecylenic, phenilacetic, monochloroacetic, trichloroacetic, glycolic, nicotinic, p-aminobenzoic, glutamic, aspartic, citric, pantothenic, crotonic, orotic, isonicotinic, p-chlorophenoxy isobutynic, picolinic, 2-pyridyl mercapto acetic, 2-pyridyl N-oxide mercapto acetic acid and N-oxyde picolinic.

However, when the active compounds carry both an amine group and a carboxylic acid function it must be used in order to break the internal salt an inorganic acid or a strong organic acid such as p-toluenesulfonic acid or trichloracetic acid.

As will be evident formula (I) above encompasses both cysteine and cysteamine derivatives. Such cysteamine derivatives can be expressed by the formula:

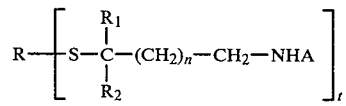

while the cysteine derivatives can be expressed by the formula:

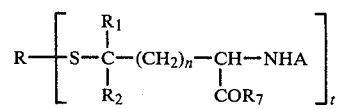

wherein R, $R_1$, $R_2$, $R_7$, A, n and t have the meanings given above.

The carrier employed with the active compound to produce the novel composition of this invention will depend for instance on the form of the product desired. Thus, the active compound can be applied topically to the skin or scalp as a solution in water, or in a mixture of water and a lower alkanol such as ethanol or isopropanol, as a cream, as a gel, as a shampoo, as an aerosol, in a reducing agent employed in the permanent waving of hair, in an oxidizing or neutralizing agent employed in the permanent waving of hair. The active compound is generally present in amounts ranging from about 0.1 to 5%, preferably about 1.5 to 2 weight percent of the total composition.

METHOD OF PREPARATION

In a general manner, active compounds of the present invention can be prepared by the reaction of a thiol, with an organic halide or with an ester of methane sulfonic acid or p-toluene sulfonic acid (Method I), or with a compound having a reactive double bond (Method II), or with an oxirane (Method IV), or with an alcohol (Method III) or with ethylene imine and its acylation and sulfonylation derivatives (Method IV).

METHOD I

The most commonly employed procedure is the substitution reaction of essentially an equimolar ratio of a thiol with an organic halide or a methane sulfonate or a p-toluene sulfonate. The thiol can be aminated or not. The reaction is carried out under conditions generally or conventionally employed for nucleophilic substitutions including, for instance, a temperature ranging from 10° to 100° C., atmospheric pressure, and employing a solvent such as water, ammonia, alcohol or dimethyl formamide in the presence of a base such as an alkali or alkaline earth hydroxide, or carbonate, an alcoholate, an alkali or alkaline earth amide or even a tertiary aliphatic amine such as triethylamine according to the following general reaction:

$$R-X + R'-SH \rightarrow R-S-R' + XH$$

$$(X = \text{halogen or } -OSO_2CH_3 \text{ or } -OSO_2C_6H_5)$$

or $$R'-X + R-SH \rightarrow R'-S-R + XH$$

The thiol R—SH or R'—SH can be prepared in situ by basic hydrolysis of an isothiouronium salt according to the following general reaction:

$$R'-S-C\begin{matrix}NH_2\\ \\ \diagdown NH_2\\ +\end{matrix} \quad X^- \xrightarrow{OH^-,RX} R'-S-R$$

METHOD I (ALTERNATIVE)

When R is an aryl radical (X=O), the halide employed is an aryldiazonium halide (Vigneaud et al, J. Biol. Chem., 1941, 138, 369 and Clarke and Inouye, J. Biol. Chem. 1931, 94.541) and the reaction follows the general equation:

$$ArN_2Cl + R'-SH \rightarrow Ar-S-R' + N_2 + HCl$$

METHOD II

The addition reaction of essentially an equimolar ratio of a thiol with a compound having a reactive double bond is well known and can be carried out, in accordance with known procedures, without a catalyst or in the presence of a peroxide such as ascaridole, benzoyl peroxide, aza bis-isobutyronitrile, or in the presence of a base such as those employed in Method I, or even a quaternary ammonium hydroxide or a secondary amine such as piperidine. Representative reaction temperatures include 10° to 100° C. and at atmospheric pressure.

The reaction is most generally effected in a medium such as alcohol, for instance, lower alkanol, water, dioxane; alone or in admixture, with a basic catalyst, so as to obtain a small quantity of thiolate to initiate the reaction.

The compound utilized having a reactive double bond does not have an amine function. It can, however, contain an amide or sulfonamide function.

The radical R can originate from either a compound having a reactive double bond (scheme 1) or from a thiol (scheme 2) when $R_3$ and A are other than hydrogen.

Scheme 1

$$\diagup C=C\diagdown + HS-\underset{R_2}{\overset{R_1}{\underset{|}{C}}}-(CH_2)_n-\underset{R_3}{\overset{|}{CH}}-NH-A \rightarrow$$

$$R-S-\underset{R_2}{\overset{R_1}{\underset{|}{C}}}-(CH_2)_n-\underset{R_3}{\overset{|}{CH}}-NHA$$

Scheme 2

$$RSH + \underset{R_2}{\overset{R_1}{\diagup}}C=C-NHA \rightarrow R-S-\underset{R_2}{\overset{R_1}{\underset{|}{C}}}-\underset{R_3}{\overset{|}{CH}}-NHA$$

(A and $R_3$ are not hydrogen)

METHOD III

The compounds of the present invention, in which the sulfur atom is linked to a disubstituted or trisubstituted carbon atom, or to a benzyl or allyl radical, can conveniently be prepared at a temperature ranging from about 50° to 150° C. and at atmospheric pressure by reaction of essentially equimolar amounts of a corresponding tertiary or secondary, benzyl or allyl alcohol, with a thiol, in the presence of a strong acid such as gaseous hydrochloric acid, p-toluene sulfonic acid, or a Lewis acid such as the etherate of boron trifluoride, in accordance with the following general reaction:

$$R''-\underset{R''''}{\overset{R''':}{\underset{|}{C}}}-OH + HS-CH_2(CH_2)_n-\underset{R_3}{\overset{|}{CH}}-NH-A \rightarrow$$

$$R''-\underset{R''''}{\overset{R''':}{\underset{|}{C}}}-S-CH_2(CH_2)_n-\underset{R_3}{\overset{|}{CH}}-NHA + H_2O$$

R'''; and R'''' only represents hydrogen when R'' represents aryl or vinyl.

METHOD IV

Another particularly useful method for preparing compounds of the present invention consists of reacting essentially equimolar amounts of a thiol with an ethylene imine or an acylation of N-sulfonylation derivative thereof at a temperature ranging from about −30° to 80° C. at ambient or atmospheric pressures according to the following equations which provide an easy method of producing the following compounds:

$$RSH + CH_2\underset{\underset{A}{\overset{|}{N}}}{\overset{}{\diagup\diagdown}}CH_2 \rightarrow R-S-CH_2-CH_2-NHA$$

$$CH_2\underset{\underset{A}{\overset{|}{N}}}{\overset{}{\diagup\diagdown}}CH_2 + HS-\underset{R_2}{\overset{R_1}{\underset{|}{C}}}-(CH_2)_n-\underset{R_3}{\overset{|}{CH}}-NHA \rightarrow$$

$$ANH-CH_2-CH_2-S-\underset{R_2}{\overset{R_1}{\underset{|}{C}}}-(CH_2)_n-\underset{NHA}{\overset{R_3}{\diagup}}CH$$

The reaction is made very easily, in a variety of solvents, chosen as a function of the solubility of the starting materials. Representative solvents include alcohols of low molecular weight and chloroform.

METHOD IV (ALTERNATE)

The β-hydroxythioethers can be prepared by an analogous procedure, by replacing the azinidine by an oxiran, and by effecting the reaction in a polar medium with a basic catalyst, as in Method I according to the following scheme:

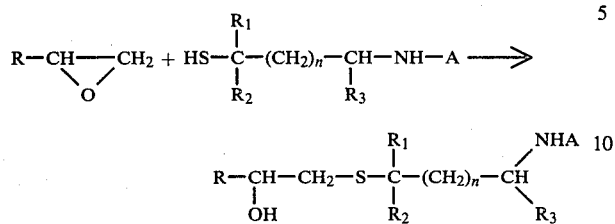

In addition to the above methods, the esters and the amides of the present invention can be prepared starting with other compounds.

Thus, esters can be obtained starting with the corresponding acid ($R_7$=OH), by reacting an appropriate alcohol therewith to give the desired ester, either at an elevated temperature in the presence of a mineral or sulfonic acid, or at a low temperature in the presence of thionyl chloride (Method V).

Amides included in the meaning of $R_3$ can be prepared simply by the reaction of ammonia, hydrazine, hydroxylamine or an appropriate amine on the ester noted above, at a temperature generally lower than 30° C. (Method IV).

The amides included in A can be conveniently prepared by the action of a halide or anhydride of a carboxylic acid to produce a carboxamide or by the action of a sulfonyl halide to produce a sulfonamide when the amide is formamide, the amide is prepared by action of formic acid. The reaction conditions most generally utilized are those of Schotten-Baumann, i.e., in water, in the presence of an alkaline hydroxide, or their rearrangement in an organic medium (aromatic hydrocarbon, generally a chlorinated solvent) in the presence of a base such as pyridine or a tertiary amine, for example, trialkylamine (Method VII).

When it is desired to prepare acylated compounds having an alcohol function, they can be obtained by the action of an amine on a lactone, the reaction being catalyzed by an alkaline alcoholate.

In the case of substituted acetamides, acetylation of the amine can often advantageously be effected by means of acetic anhydride in an acetic acid medium in the presence of concentrated sulfuric acid.

It will be noted, however, that the majority of the amides included in the meaning of A are in addition easily produced by one or more of Methods I–IV.

Finally, compounds of the type where A equals —$CONH_2$ are prepared by the action, in an aqueous or aqueous alcoholic medium, of an alkaline cyanate on a compound of the type A=H, in the presence of an equivalent amount of mineral acid, preferably, hydrochloric acid (Method VIII), the starting compound being obtained according to Methods I–IV.

The preparation of the salts of the active compounds is generally carried out by first dissolving the acid in an appropriated solvent and then pouring to this solution either a solution of the active compound in the same solvent or the active compound alone. The solvent must not be a solvent of the salt.

To prepare hydrochlorides, it is more convenient to dissolve the active compound in an appropriated solvent and then to bubble in the solution a slight stream of hydrogen chloride.

REPRESENTATIVE EXAMPLES OF PREPARING ACTIVE COMPOUNDS ACCORDING TO THE FOREGOING GENERAL REACTIONS:

EXAMPLE 1

N-(2-benzylthioethyl)nicotinamide: (Method VII)

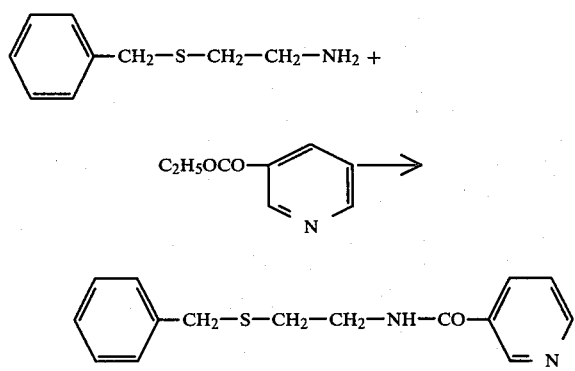

30 grams of ethyl nicotinate and 80 grams of 2-benzylthio ethylamine are heated for 12 hours at 170°–180° C. The ethane liberated during the reaction is removed by means of a Dean Stark apparatus. After cooling, the reaction mixture is dissolved in 400 cc of carbon tetrachloride; by addition of petroleum ether, the N-(2-benzylthioethyl)nicotinamide crystallizes: 47 g. By crystallization in a mixture of carbon tetrachloride and cyclohexane, there are recovered colorless crystals of the above product melting at 79° C.

| | Analysis: | |
|---|---|---|
| | N | S |
| Calculated, % | 10.3 | 11.8 |
| Found, % | 10.4 | 11.9 |

By bubbling HCl gas into an acetone solution of the above product, the hydrochloride thereof is recovered, which melts at 135° C.

EXAMPLE 2

5-p-toluenesulfonamido 3-thia hexanedioic acid (Method VII)

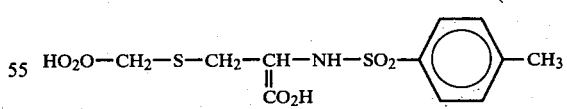

17.9 grams of 3-carboxymethylthio alanine are dissolved in 200 cc of normal soda. There are added under agitation 24 grams of p-toluene sulfonyl chloride then, in 3 hours, 100 cc of normal soda. The suspension is agitated again for 5 hours at ambient temperature, then filtered. The filtrate, acidified with HCl, is extracted with ethyl acetate. After evaporation of the ethyl acetate, there remains a yellow solid which crystallizes in water. 20 grams of the above product in crystalline form are obtained having a melting point of 152° L C.

| | Analysis: | | |
|---|---|---|---|
| | C | H | S |
| Calculated, % | 43.23 | 4.53 | 19.23 |
| Found, % | 43.19 | 4.48 | 19.24 |

EXAMPLE 3

2-(2-p-toluenesulfonamido ethylthio)pyridine N-oxide (Method VII)

(Method VII)

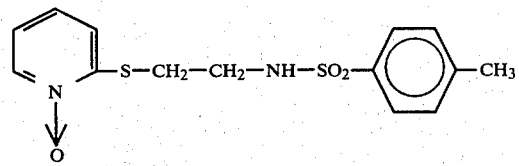

To a solution of 4.12 g of 2-β-aminoethylthio pyridine N-oxide hydrochloride in 60 cc of water, there are added 4 cc of 5 N soda, then 3.8 g of p-toluenesulfonyl chloride. The mixture is agitated for 5 hours at ambient temperature. The pH is maintained at 9.5 by the addition of normal soda. The precipitate is filtered and crystallized in aqueous ethanol. Yield=88%. Fusion point: 201° C.

| | Analysis: | |
|---|---|---|
| | N | S |
| Calculated, % | 8.64 | 19.77 |
| Found, % | 8.77 | 19.85 |

EXAMPLE 4

3-(2-pyridyl methylthio)alanine (Method I)

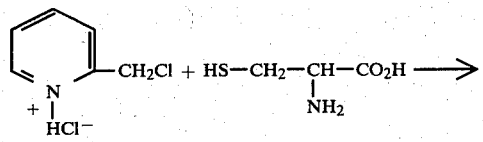

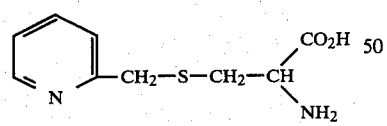

There are added, over a 15 minute period, 96 cc of 10 N soda to an aqueous solution of 54 g of cysteine hydrochloride. The solution obtained is treated by a cation exchange resin and the product absorbed on the resin is liberated with an ammoniacal solution. The eluate is evaporated and the residue is crystallized in a mixture of methanol and isopropyl ether. There are thus recovered 49 g of whitish crystals melting at 190° C.

| | Analysis: | |
|---|---|---|
| | N | S |
| Calculated, % | 13.26 | 15.10 |
| Found, % | 13.23 | 15.32 |

EXAMPLE 5

3-o-chlorobenzylthio alanine and the corresponding methyl ester (Method I)

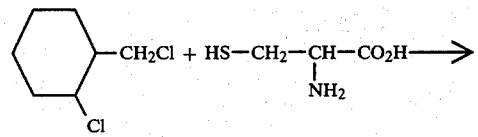

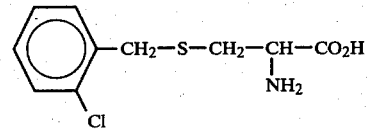

In 400 cc of ethanol containing 6.9 g of sodium, there are introduced 15.75 g of cysteine hydrochloride, then a solution of 16 g of o-chlorobenzyl chloride in 20 cc of ethanol. The mixture is heated for 1 hour at 50° C. After cooling, there are added 400 cc of water and 30 cc of acetic acid. The product crystallizes and is filtered and washed with water. Yield: 20.8 g. Fusion point is 220° C.

| Analysis: | C | H | N |
|---|---|---|---|
| Calculated, % | 48.87 | 4.92 | 5.70 |
| Found, % | 48.61 | 4.68 | 5.42 |

15 grams of the product obtained above are put into suspension in 15 cc of methanol, in which there is bubbled a stream of dry gaseous HCl for thirty minutes. The reaction mixture is left standing for 2 hours at ambient temperature, evaporated to dryness, the oily residue being dissolved in 30 cc of methanol. The product is crystallized by the addition of diethyl oxide. Yield=90%. Fusion point 150° C.

| Analysis: | C | H | N |
|---|---|---|---|
| Calculated, % | 44.60 | 5.10 | 4.72 |
| Found, % | 44.52 | 5.32 | 4.65 |

EXAMPLE 6

2,2'-thio diethylurea (Method I and VIII)

Method I:

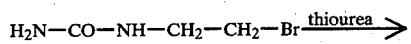

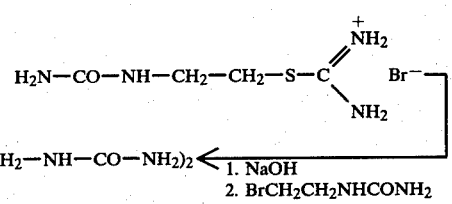

There are heated under reflux for 30 minutes, 66.3 g of thiourea and 145.6 g of β-bromoethylurea in 600 cc of isopropanol. The precipitate (185 g) is filtered, washed with isopropanol and dissolved in 900 cc of water. There is added to this solution during a 15 minute period, a solution of 30.45 g of soda in 150 cc of water and the resulting mixture is heated in a boiling water-bath for one hour under nitrogen. The water bath is removed and there are again introduced 150 cc of a soda solution (30.45 g soda), then a solution of 127.15 g of β-bromoethylurea in 150 cc of water.

The reaction mixture is left standing overnight at ambient temperature. The crystallized product is then filtered, yielding 126 g of white product melting at 234° C.

Method VIII:

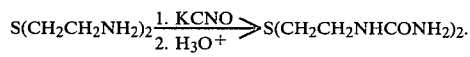

To a solution of 92.4 g of 2,2'-thio diethylamine in 70 cc of water, there are added with agitation 133 cc of 11.6 N hydrochloric acid while cooling so as to maintain the temperature below about 25° C. Then there is added sufficiently rapidly, a solution of 127 g of potassium cyanate (98%) in 150 cc of water. The reaction mixture is left standing overnight and the resulting precipitate is filtered, dried and crystallized in water, yielding 128 g of white crystals, the fusion point of which is 234° C.

| Analysis: | N | S |
| --- | --- | --- |
| Calculated, % | 27.18 | 15.53 |
| Found, % | 27.15 | 15.32 |

EXAMPLE 7

3,3'(1,4 dithio butene-2-diyl)dialanine (Method I)

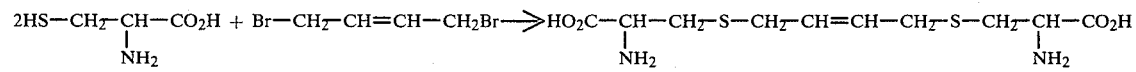

There is added dropwise a solution of 21.4 g of 1,4 dibromo butene-2 in 200 cc of ethanol to a solution of 35.10 g of the hydrochloride of cysteine monohydrate and 40 cc of 10 N soda in 200 cc of water and 300 cc of ethanol. The mixture is agitated for 6 hours at ambient temperature. The precipitate which forms is filtered and crystallized in a mixture of methanol and water. There is obtained a yield of 97% of a white solid.

| Analysis: | C | H | N |
| --- | --- | --- | --- |
| Calculated, % | 40.79 | 6.16 | 9.51 |
| Found, % | 40.74 | 6.23 | 9.23 |

EXAMPLE 8

3-β-ureidoethylthio alanine (Method I)

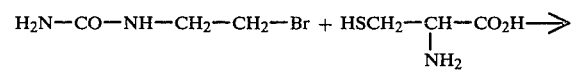

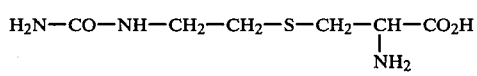

26.25 g of cysteine hydrochloride and 27.83 g of β-bromoethylurea are dissolved in 150 cc of water under nitrogen. A solution of 13.35 g of soda in 30 cc of water is added during a 40 minute period and the mixture is heated for 3 hours at 50° C. After cooling, there is added to the solution, four times its volume of water and the resulting mixture is passed over a cation exchange resin. After washing with water, the product fixed on the resin is eluted with an ammoniacal solution. The eluate is evaporated to dryness and the residue is crystallized in an aqueous methanol solution. There are obtained 19.5 grams of the white product melting at 220° C. with decomposition.

| Analysis: | C | H | S |
| --- | --- | --- | --- |
| Calculated, % | 34.80 | 6.28 | 15.46 |
| Found, % | 34.84 | 6.20 | 15.62 |

EXAMPLE 9

3-(4-methoxycarbonylbutylthio)alanine hydrochloride (Method I)

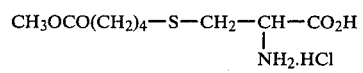

To a solution of 8.77 g of cysteine hydrochloride monohydrate in 150 cc of methanol, there are added, successively, 7.6 g of potassium, then, during a 30 minute period, 10.45 g of methyl ω-bromopentanoate.

The mixture is heated for 6 hours under reflux, then filtered after cooling. The precipitate is dissolved in a minimum amount of water and the solution obtained is acidified with concentrated hydrochloric acid. The desired product precipitates (10.2 g). It can be crystallized in methanol by adding diethyl oxide. White crystals are produced which melt at 160° C.

| Analysis: | N | S |
| --- | --- | --- |
| Calculated, % | 5.16 | 11.85 |
| Found, % | 5.46 | 12.03 |

EXAMPLE 10

2-(5-methoxycarbonyl pentylthio)ethylamine hydrochloride (Method I)

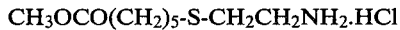

There are added successively, to a solution of 2.6 g of potassium in 100 cc of methanol, 4.5 g of β-mercaptoethylamine hydrochloride, then slowly 8.2 g of methyl ω-bromohexanoate.

The mixture is heated for 3 hours under reflux. After cooling, it is acidified with gaseous hydrochloric acid and filtered. The filtrate is evaporated to dryness and the oily residue (8 g) crystallizes rapidly. The product melts at 80° C. after crystallization in a mixture of methanol and diisopropyl oxide.

| Analysis: | Cl |
|---|---|
| Calculated, % | 14.70 |
| Found, % | 14.78 |

EXAMPLE 11
3-(2-p-toluenesulfonamidoethylthio)alanine (Method I)

p-CH$_3$—C$_6$H$_4$—SO$_2$—NH—CH$_2$—CH$_2$—O—SO$_2$—C$_6$H$_4$—p-CH$_3$ +

HS—CH$_2$—CH—CO$_2$H ⟶
      |
     NH$_2$ p-CH$_3$—C$_6$H$_4$—SO$_2$—NH—CH$_2$—CH$_2$—S—CH$_2$—CH—CO$_2$H
                                                                                      |
                                                                                  NH$_2$

To a suspension of 17.55 g of cysteine hydrochloride monohydrate and 37 g of 2-p-toluenesulfonamido ethyl p-toluene sulfonate in 500 cc of methanol, there is added, during a one hour period, at 50° C. a solution of 19.6 g of potassium at 85% in 500 cc of methanol.

The potassium chloride and potassium p-toluene sulfonate are removed by filtration. The mother liquor is evaporated to dryness, leaving an oil which is mixed with water and acidified with acetic acid. The product precipitates and is crystallized in water. Yield is 29 g. Fusion point is 215° C.

EXAMPLE 12
2-methylthioethylammonium phenylacetate (Method I)

CH$_3$S—CH$_2$—CH$_2$—N$^+$H$_3$O$_2^-$C—CH$_2$—C$_6$H$_5$

There are added, progressively and with intense agitation, 41 g of 2-bromo ethylamine hydrobromide to a solution of sodium methanethiolate in ethanol (starting with 9.6 g of methane thiol and 9.2 g sodium).

The mixture is agitated for one hour at ambient temperature, then heated under reflux for 30 minutes. After cooling, the mixture is diluted with 200 cc of ether and then filtered to remove therefrom the mineral salts. The filtrate is concentrated and the resulting oily residue is fractionated. The fraction distilling at 42° C. under 16 mm Hg, is recovered and yields 13.6 g (75%) of 2-methylthioethylanine which are added, in a solution of ether (300 cc), to a solution of phenyl-acetic acid (0.15 mol) in the same solvent. The salt formed crystallizes, in proportion to the addition, in the form of white needles (33.5 g) which are purified by crystallization in ethyl acetate. Yield=92%. Fusion point: 92°-94° C.

| Analysis: | N | S |
|---|---|---|
| Calculated, % | 6.16 | 14.10 |
| Found, % | 6.11 | 14.01 |

EXAMPLE 13
3-(9,11dihydroxy 10,10-dimethyl 4,8-dioxo 3,7-diaza undecylthio)alanine-(Method IV)

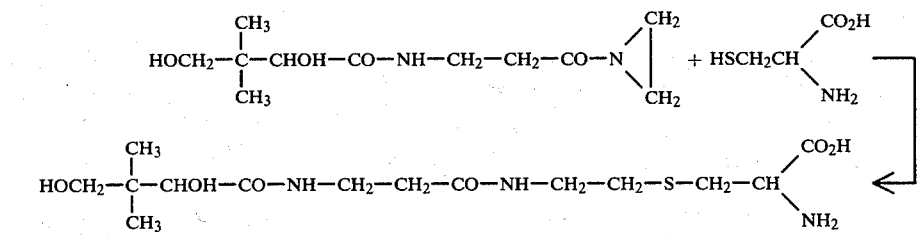

10 g of calcium pantothenate are dissolved in 10 cc of water. To this solution are added, in succession, 2.66 g of oxalic acid in a minimum of water and 10 cc of triethylamine. The calcium oxalate formed is removed by filtration. There is obtained triethylamine pantothenate in the form of an oil by concentrating the filtrate to dryness.

This salt is dissolved in 25 cc of anhydrous dimethyl formamide and the solution is cooled to −5° C. Then dropwise, while maintaining the temperature at −5° C., there is added a solution of 4.1 g of ethyl chloroformate.

The mixture is added dropwise to a solution of 25 g ethyleneimine and 5 g of triethylamine in 50 cc of ethyl acetate while maintaining the temperature at −5° C. The mixture is agitated for 20 minutes at −5° C.

During a period of about 15 minutes, there is added a filtered solution of 6.6 g of cysteine hydrochloride and 4.2 g of triethylamine in 20 cc of dimethyl formamide. After 30 minutes at 0° C., the solution is filtered and the filtrate is evaporated to dryness under a vacuum. The oily residue is dissolved in ethyl ether and after standing, crystallizes in the form of a white hygroscopic product, the fusion point of which is 75°-80° C. Yield-75%.

The proportion of carboxylic acid and amine functions correspond to theory.

EXAMPLE 14
2-amino 4-thia nonadioic acid (Method II)

HO$_2$C—CH—CH$_2$SH + CH$_2$=CH—(CH$_2$)$_2$—CO$_2$H ⟶
       |
      NH$_2$

HO$_2$C—CH—CH$_2$—S—(CH$_2$)$_4$—CO$_2$H
       |
      NH$_2$ 10 g of allylacetic acid are added dropwise to 15.75 g of cysteine hydrochloride. Under intense agitation, there are added 10 mg of benzoyl peroxide. The mixture becomes heated and liquifies and is maintained for 1 hour at 80° C. After cooling, it is dissolved in 50 cc of 2 N soda. The precipitate that forms is filtered and washed with water. Yield: 16.5 g. After crystallization in dilute hydrochloric acid, the product melts at 230° C. with decomposition.

The proportion of carboxylic acid function corresponds to theory.

EXAMPLE 15

Bis[2-(2,2-dimethoxyethylthio)ethylamine]oxalate
(Method I)

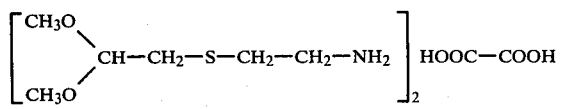

To a solution of 4.6 g of sodium in 150 cc of ethanol, there are added 11.35 g of β-mercaptoethylamine hydrochloride, then, dropwise 16.9 g of the bromide of 2,2'-dimethoxyethyl bromoacetaldehyde dimethylacetal.

The mixture is heated for 2 hours under reflux. The mineral salts are filtered after cooling and the mother liquor is concentrated. The oily residue is distilled in 17 mm Hg at 125°–130° C. Yield=74%.

The 12.2 g of 2-(2,2-dimethoxyethylthio)ethylamine obtained above are dissolved in 50 cc of ethanol and added to a solution of 4.65 g of the dihydrate of oxalic acid. The salt formed crystallizes by addition of ethyl ether, after cooling. By crystallization in 2-propanol and ethyl ether, white crystals are obtained. Fusion point: 170°–172° C. Weight: 28.6 g

| Analysis: | N | S |
|---|---|---|
| Theory, % | 6.66 | 15.25 |
| Found, % | 6.58 | 15.18 |

EXAMPLE 16

2-(2-p-methoxyphenyl 2-propylthio)ethylamine hydrochloride (Method III)

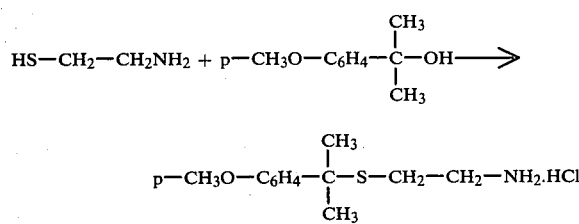

To a solution of 11.25 g of β-aminoethylthio in 50 cc acetic acid there are added successively 15.42 g of p-methoxy phenyl dimethyl carbinol and a solution of boron trifluoride in acetic acid. The mixture is heated 30 minutes at 60° C., then cooled. This solution is added dropwise to a 10% solution of sodium acetate, which is extracted three times with ethyl ether and dried over sodium sulfate. By bubbling gaseous hydrochloric acid in the etherified solution, the product is produced as a white precipitate. Fusion point with decomposition: 172°–174° C. Yield: 62%.

| Analysis: | C | H | N |
|---|---|---|---|
| Theory, % | 55.05 | 7.70 | 5.35 |
| Found, % | 54.98 | 7.85 | 5.21 |

EXAMPLE 17

2-acetamido 3-(2,4-dichlorobenzylthio)propionic acid
(Method I and VII)

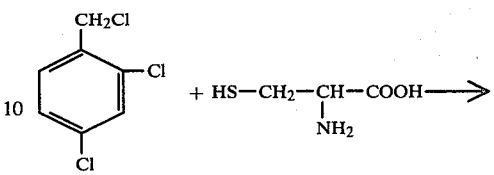

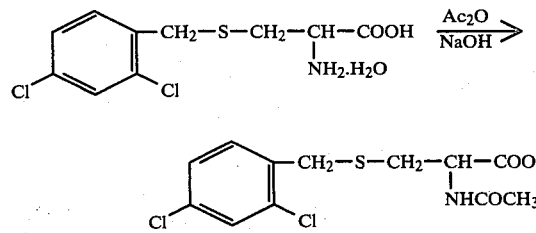

To a solution of 6.9 g of sodium in 400 cc of absolute ethanol, there are added, successively, 15.75 g of cysteine hydrochloride and 19.54 g of 2,4-dichloro benzyl chloride.

Then the mixture is heated at 50° C. for a period of one hour. By adding 600 cc of water and 30 cc of acetic acid, the product crystallizes in the form of needles. Fusion point 205°–210° C.

24.5 g of this product, 2-amino 3-(2,4-dichlorobenzylthio)propionic acid, are acetylated in accordance with the conventional Schatten-Baumann reaction. There is obtained a precipitate which is crystallized in 40% ethanol, weight: 23.85 g. Fusion point: 134°–135° C.

| Analysis: | C | H | N |
|---|---|---|---|
| Theory, % | 44.73 | 4.06 | 4.34 |
| Found, % | 44.78 | 4.17 | 4.35 |

EXAMPLE 18

3-[Bis-(p-methoxy phenyl) 3-methylthio]alanine
(Method III)

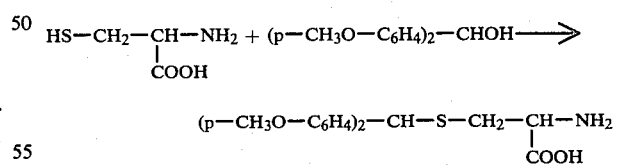

A solution of 17.56 g of cysteine hydrochloride monohydrate in 85 cc of acetic acid is heated with agitation at 60° C. Then there is added, successively, 24.4 g of bis-(p-methoxyphenyl)carbinol and 20.7 g of boron trifluoride in acetic acid. The mixture is heated at 80° C. for a period of 15 minutes, then cooled to 10° C. Then, by adding a solution of 48 g of sodium acetate in 50 cc of water and 150 cc of ethanol, the product precipitates. After crystallization in a mixture of water and dimethylformamide, there are obtained white crystals, the fusion point of which is 209°–211° C. Yield: 85%.

| Analysis: | C | H | N |
|---|---|---|---|
| Theory, % | 62.22 | 6.09 | 4.03 |
| Found, % | 62.38 | 6.15 | 4.22 |

EXAMPLE 19

2-allylthioethylammonium malate

CH$_2$=CH—CH$_2$—S—CH$_2$—CH$_2$—N$^+$H$_3$O$_2$—C—CH(OH)CH$_2$—COOH (Method I)

4.2 2 g of allyl bromide are added dropwise to a solution of 22.7 g of β-aminoethylthio in 150 cc of ethanol containing 9.2 g of metallic sodium. The mixture is heated under reflux for 1 hour. The resulting oil phase is decanted and is dissolved by adding ether thereto in order to eliminate by filtration the mineral salts. The filtrate is concentrated under vacuum, leaving an oily residue. Weight: 38.1 g. The oily residue is dissolved in 100 cc of absolute ethanol and 43.5 g of malic acid are added with agitation in small portions. By adding ether, the product forms as a white precipitate which, after crystallization in 2-propanol, melts at 94° C. Yield: 65%.

| Analysis: | N | S | C | H |
|---|---|---|---|---|
| Theory, % | 5.57 | 12.76 | 43.01 | 6.81 |
| Found, % | 5.56 | 12.66 | 43.04 | 6.90 |

EXAMPLE 20

2-amino 4-β-aminoethylthio butyric acid (Method I)

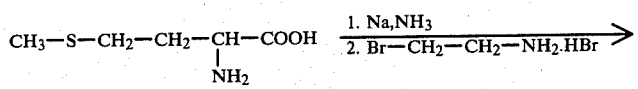

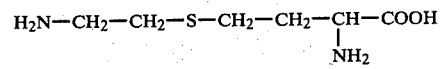

There are added, in small amounts, 21.52 g of sodium to a suspension of 40 g of methionine in 1.5 l of liquid ammonia. After the addition, the mixture is maintained under agitation for 4 hours. There is then added to the mixture sufficient ammonium chloride to decolorize the solution. The ammonia is evaporated overnight at ambient temperature and the white residue is dissolved in 200 cc of water. There is added, over a 2-hour period, a solution of 55 g of 2-bromo ethylamine hydrobromide in 300 cc of water. The mixture is agitated for 3 hours at 20° C. and then for 3 hours at 50° C. The reaction product is then treated with DOWEX Resin 50 W, and then eluted by means of an ammoniacal solution. The eluate is concentrated under vacuum. The solid residue is admixed with 75 cc of water, neutralized with 52 cc of 6 N hydrochloric acid and treated with animal charcoal. There is obtained after filtration a colorless solution which is then concentrated under vacuum. The solid residue is crystallized in a mixture of water, methanol, acetone and is in the form of white crystals (38 g) melting at 216°–217° C.

| Analysis - C$_6$H$_{15}$ClN$_2$O$_2$S | | | | |
|---|---|---|---|---|
| | C | H | N | HCl |
| Calculated, % | 33.66 | 7.03 | 13.05 | 17.03 |
| Found, % | 33.61 | 7.18 | 13.08 | 17.08 |

EXAMPLE 21

S-β-aminoethyl mercaptobutyric acid (Method I)

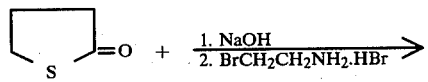

H$_2$NCH$_2$CH$_2$SCH$_2$CH$_2$CH$_2$COOH

A solution of 51 g of 2-thiolannone in 50 cc of methanol is added to a solution of 150 cc of 10 N soda, 400 cc of water and 500 cc of methanol. In the resulting solution, there are introduced, in several portions, 103 g of β-bromoethylanine hydrobromide. The mixture is heated under reflux for 3 hours. The solution is treated with an ion exchange resin in hydrogen form, in accordance with conventional procedures. The concentrated eluate provides a solid residue which is washed in ethanol and filtered. Yield: 62.5 g. Fusion point: 171° C.

The proportion of acid and amine functions conform to theory.

EXAMPLE 22

S-β-ureidoethylmercaptoacetic acid (Methods I and VIII)

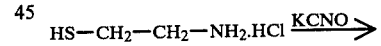

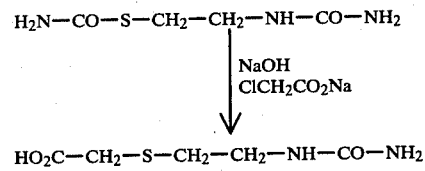

To a solution of 34.1 g of β-mercaptoethylamine hydrochloride in 200 cc of water there are added a solution of 24.3 g of potassium cyanate in 80 cc of water, then 36 g of sodium monochloroacetate in 200 cc of water. The solution is heated at 50° C. for 2 hours while maintaining the pH at 6 by the addition of 2 N soda. The mixture is then acidified, concentrated to dryness and washed with a mixture of water and ethanol. After filtration, there are produced 42 g of the product which melts at 135° C.

| Analysis: | C | H | N | S |
|---|---|---|---|---|
| Calculated, % | 33.69 | 5.65 | 15.72 | 17.99 |

| Analysis: | C | H | N | S |
|---|---|---|---|---|
| Found, % | 33.79 | 5.67 | 15.62 | 18.07 |

EXAMPLE 23

2-methoxycarbonylmethylthioethylamine hydrochloride (Method V)

CH₃O—CO—CH₂—S—CH₂—CH₂—NH₂.HCl 13.5 g of S-(β-aminoethyl)mercaptoacetic acid and 10.8 g of 2,2-dimethoxy propane are added, successively, to a solution of 7.3 g of gaseous hydrochloric acid in 20 cc of methanol. The solution is permitted to stand for 12 hours at ambient temperature. The flakes formed (17.5 g) are filtered and washed with ethyl acetate. Fusion point=100° C.

| Analysis: | Cl |
|---|---|
| Calculated, % | 19.1 |
| Found, % | 19.2 |

EXAMPLE 24

N-(2-benzylthioethyl)2,4-dihydroxy 3,3-dimethyl butyramide (Method VII)

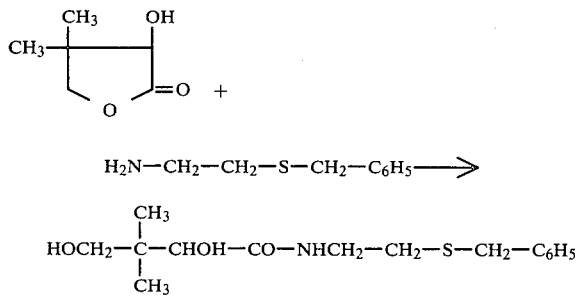

13 g of pantolactone with a few drops of a methanol solution of sodium methylate are added to a solution of 16.7 g 2-benzylthio ethylamine in 50 cc of ethanol. The mixture is heated for 6 hours at 60°–65° C.

After cooling, the product is crystallized by addition of diethyl oxide. White crystals (23.8 g) melt at 70° C.

EXAMPLE 25

2-β-hydroxyethylthioethylamine hydrochloride (Method IV)

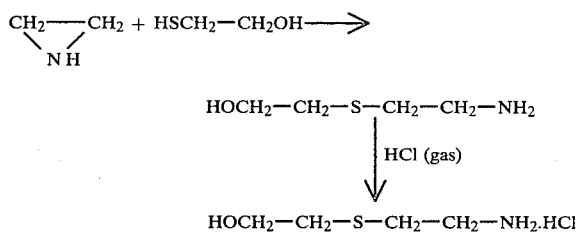

There are added in 1 hour, 39 g of 2-mercapto ethanol in 50 cc of ethanol to a solution of 21.5 g of ethyleneimine in 100 cc of ethanol. The mixture is maintained for 10 hours at 40° C. and then concentrated to dryness. The oily residue (56 g) is fractionated under vacuum (1.5 mm Hg) and the fraction distilling at 113°–116° C. (48 g) is recovered.

By the action of gaseous hydrochloric acid on an ethanol solution of the distilled amine, there is obtained the hydrochloride in the form of crystals (59 g) which melt at 45°–48° C.

| Analysis: | HCl |
|---|---|
| Calculated, % | 23.15 |
| Found, % | 23.10 |

EXAMPLE 26

3,3′-(2′,2-sulfonyl diethylthio)dialanine and the N,N′-diacetyl derivative thereof. (Method II and VII)

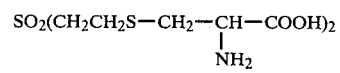

To a solution of 70.2 g of cysteine hydrochloride monohydrate in 300 cc of water, there are added, successively, 53 cc of 8 N soda, 0.5 cc of concentrated ammonia and after 30 minutes, a solution of 23.6 g of divinyl sulfone in 300 cc of water. After two hours under agitation, the reaction mixture is filtered and the precipitate (67 g) is washed with water and with ethanol.

| | Analysis: | | |
|---|---|---|---|
| | C | H | N |
| Calculated, % | 33.31 | 5.59 | 7.77 |
| Found, % | 32.99 | 5.56 | 7.72 |

21.6 g of the precipitate obtained above are dissolved in 30 cc of water and 15 cc of 8 N soda. To this solution, there are added, successively, 60 cc of acetic anhydride and 112.8 cc of 8 N soda.

Agitation of the mixture is continued for some time and it is acidified with 147.6 cc of 10 N hydrochloric acid. The precipitate formed in filtered and washed with water. Yield: 21.42 g. Fusion point: 196° C.

| | Analysis: | | |
|---|---|---|---|
| | C | H | N |
| Calculated, % | 37.82 | 5.44 | 6.30 |
| Found, % | 37.38 | 5.43 | 6.35 |

B. Examples Of Compositions Containing Active Compounds And Their Use In Accordance With This Invention The compositions of the present invention as stated above can be provided in various forms depending, for instance, on the choice of carrier admixed with the active compound. The following examples illustrate representative carriers employed to produce the novel compositions of this invention, all of which, of course, effectively reduce excessive secretion of sebum from the skin and/or scalp.

1. Carrier-Water or Aqueous-lower alkanol solution.

EXAMPLE 27

A composition in accordance with the invention is prepared by mixing 1.5 g of 3-tritylthio-alanine hydrochloride with 100 cc of 50% aqueous ethyl alcohol solution containing 0.1 g of perfume and 0.1 g of a coloring agent.

EXAMPLE 28

A composition in accordance with the invention is prepared by dissolving 2 g of 2-amino 4-thia heptanedioic acid in 100 cc of perfumed distilled water, the pH being adjusted to 7 by adding triethanolamine.

EXAMPLE 29

A composition in accordance with the invention is prepared by dissolving 2 g of methyl S-diphenylmethyl-1-cysteinate and 0.1% of coloring agent in 100 cc of 60% aqueous ethyl alcohol solution.

EXAMPLE 30

A composition in accordance with the invention is obtained by dissolving 0.75 g of 3-($\beta$-hydroxy ethylthio) alanine in 100 cc of a 50% aqueous ethyl alcohol solution containing 0.1% of perfume and 0.1% of coloring agent.

EXAMPLE 31

A lotion in accordance with the invention is prepared by dissolving 0.75 g of 5-amino 3-thia dimethyl hexanedioate hydrochloride and 0.1 g of perfume in 100 cc of a 50% aqueous ethyl alcohol solution.

EXAMPLE 32

A composition according to the invention is prepared by dissolving 1.5 g of S-$\beta$amino ethyl mercapto acetic acid in 100 cc of perfumed distilled water.

EXAMPLE 33

A composition according to the invention is made by preparing the following mixture:

| | |
|---|---|
| S—($\beta$ amino ethyl) mercapto acetic acid | 0.54 g |
| Methionine | 0.50 g |
| Distilled water, q.s.p. | 100 cc |

EXAMPLE 34

A composition for treating a greasy scalp according to the invention is made by dissolving 1.5 grams of the hydrochloride of 2-trityl thio ethylamine having the formula $(C_6H_5)_3$—C—S—$CH_2$—$CH_2$—$NH_2$.HCl in 100 cc of 50% solution of water and ethanol.

EXAMPLE 35

A composition for treating a greasy scalp according to the invention is made by dissolving:

| | | |
|---|---|---|
| Hydrochloride of 2-(2 naphtyl thio) ethyl ammonium disuccinate | 1.5 | g |
| Methionine | 0.10 | g |
| Distilled water, q.s.p. | 100 | cc |

EXAMPLE 36

A composition for treating a greasy scalp according to the invention is prepared by dissolving:

| | | |
|---|---|---|
| Hydrochloride of 2-benzylthio ethylamine | 0.82 | g |
| Perfumed distilled water, q.s.p. | 100 | cc |

EXAMPLE 37

A composition for treating a greasy scalp according to the invention is made by preparing the following mixture:

| | | |
|---|---|---|
| Hydrochloride of 2-benzyl thio ethylamine | 1.5 | g |
| Methionine | 0.5 | g |
| Perfumed distilled water, q.s.p. | 100 | cc |

EXAMPLE 38

A composition for treating a greasy scalp according to the invention is prepared as follows:

| | | |
|---|---|---|
| Hydrochloride of S—(3-amino propyl) mercapto acetic acid | 1.5 | g |
| Perfumed distilled water | 100 | cc | to which is added:

| | |
|---|---|
| Carboxyvinyl polymer-carboxypolymethylene, sold under the trade name CARBOPOL 940 | 125 g |

The whole mixture is made alkaline by adding a drop of ammonia to obtain a pH between 8.0 and 8.2.

This produces a gel which can be applied at the rate of about 0.5 g of gel on scalp moderately affected by excessive secretion of sebum.

EXAMPLE 39

A grooming lotion for gentlemen is prepared by mixing:

| | |
|---|---|
| Hydrochloride of 2-trityl thio ethylamine | 0.75 g |
| Dimethylhydantoin formaldehyde resin | 0.5 g |
| Dimethyl-dilaurylammonium chloride | 0.5 g |
| Perfume | 0.1 g |
| Ethanol | 50 cc |
| Water, q.s.p. | 100 cc |

EXAMPLE 40

A lotion is prepared by mixing:

| | |
|---|---|
| Hydrochloride of 2-benzyl thio ethylamine | 0.7 g |
| Calcium pantothenate | 0.25 g |
| p-aminobenzoic acid | 0.25 g |
| polyethyleneglycol (M.W. 300) | 5.0 g |
| Perfume | 0.1 g |
| Ethanol | 50 cc |
| Water, q.s.p. | 100 cc |

EXAMPLE 41

A grooming gel is prepared by mixing:

| | |
|---|---|
| Hydrochloride of 2-trityl thio ethylamine | 0.25 g |
| Methyl pantothenate | 0.2 g |
| Carboxy vinyl polymer-carboxypolymethylene, sold under the trade name "Carbopol 940" | 0.5 g |
| Polyvinyl pyrrolidone (M.W. 40,000) | 3.0 g |
| Propyleneglycol | 10.0 g |
| Triethanolamine, q.s.p. | pH 8 |
| Perfume | 0.1 g |
| Ethanol | 20 cc |
| Methyl parahydroxybenzoate, sold under the trade name "Nipagin M" | 0.10 g |
| n-propyl-p-hydroxybenzoate, sold under the trade name "Nipasol" | 0.10 g |
| 2-bromo, 2-nitro 1–3 propanediol | 0.3 g |
| $H_2O$, q.s.p. | 100 cc |

EXAMPLE 42

A grooming liquid gel is prepared by mixing:

| | |
|---|---|
| Hydrochloride of 2-amino 4-thia decanedioic acid | 0.1 g |
| Carboxy vinyl polymer-carboxy polymethylene, sold under the trade name "Carbopol 940" | 0.45 g |
| Polyvinyl pyrrolidone (M.W. 40,000) | 2.0 g |
| Lanolin oxyethylenated with 16 moles ethylene oxide | 1.0 g |
| Polyethyleneglycol (M.W. 300) | 5.0 g |
| Methyl parahydroxybenzoate, sold under the trade name "Nipagin M" | 0.10 g |
| n-propyl-p-hydroxybenzoate, sold under the trade name "Nipasol" | 0.10 g |
| Perfume | 0.1 g |
| Triethanolamine, q.s.p. | pH 8 |
| $H_2O$, q.s.p. | 100 cc |

EXAMPLE 43

A dermal cream is prepared by mixing:

| | |
|---|---|
| 3-($\beta$-ureido ethyl thio) alanine | 5 g |
| Cetylstearyl alcohol oxyethylenated with 15 moles ethylene oxide | 7.0 g |
| Silicone oil | 1.0 g |
| Diethyleneglycol stearate | 6.0 g |
| Methyl parahydroxybenzoate, sold under the trade name "Nipagin M" | 0.10 g |
| n-propyl-p-hydroxybenzoate, sold under the trade name "Nipasol" | 0.10 g |
| $H_2O$, q.s.p. | 100 cc |

EXAMPLE 44

A dermal milk is prepared by mixing:

| | |
|---|---|
| -3-(2,4-dichlorobenzylthio) alanine | 0.5 g |
| Carboxy vinyl polymer-carboxy polymethylene, sold under the trade name "Carbopol 934" | 0.375 g |
| Isopropylic esters of fatty acids of lanolin | 1.0 g |
| Lanolin oxyethylenated with 16 moles ethylene oxide | 2.5 g |
| Cetyl-stearyl alcohol oxyethylenated with 15 moles ethylene oxide | 3.0 g |
| Substituted alkyl amide | 2.0 g |
| Ethanol | 20 cc |
| Triethanolamine, q.s.p. | pH 8 |
| Methyl parahydroxybenzoate, sold under the trade name "Nipagin M" | 0.10 g |
| n-propyl-p-hydroxybenzoate, sold under the trade name "Nipasol" | 0.10 g |
| $H_2O$, q.s.p. | 100 cc |

EXAMPLE 45

A composition according to the invention is prepared by dissolving in 100 cc of perfumed distilled water, 5 g of 2-benzyl thio ethylamine hydrobromide.

EXAMPLE 46

A lotion according to the invention is prepared by dissolving 3 g of 2-(t-butyl thio) ethylamine in 100 cc of 50% water-ethanol solution.

EXAMPLE 47

A lotion according to the invention is prepared from the following composition:

| | |
|---|---|
| dihydrochloride of 2-(2 pyridyl N—oxide thio) ethylamine | 1.0 g |
| Perfumed distilled water, q.s.p. | 100 cc |

EXAMPLE 48

A lotion according to the invention is prepared from the following:

| | | |
|---|---|---|
| Hydrochloride of 2-thenyl thio ethylamine | 1.5 | g |
| Methionine | 0.75 | g |
| Perfumed distilled water, q.s.p. | 100 | cc |

EXAMPLE 49

A grooming lotion for gentlemen is prepared according to the invention, with the following composition:

| | | |
|---|---|---|
| Nicotinate of 2-benzyl thio ethylammonium | 1.0 | g |
| Dimethylhydantoin formaldehyde | 0.5 | g |
| Dimethyldilaurylammonium chloride | 0.5 | g |
| Perfume | 0.1 | g |
| Ethanol | 60 | cc |
| Water, q.s.p. | 100 | cc |

EXAMPLE 50

A lotion according to the invention having the following composition is prepared:

| | | |
|---|---|---|
| Malate of 2-benzylthio ethylammonium | 1.3 | g |
| Polyethyleneglycol (M.W. 300) | 5.0 | g |
| Perfume | 0.1 | g |
| Water, q.s.p. | 100 | cc |

EXAMPLE 51

A composition containing 1.5 g of 2-(2 pyridyl methylthio) ethylamine dihydrochloride in 100 cc of a 50% aqueous ethanol solution.

EXAMPLE 52

A composition containing 1 g of 2-methyl thio ethylammonium phenylacetate in 100 cc of perfumed distilled water.

EXAMPLE 53

A composition containing 0.8 g of 2($\beta$-hydroxyethylthio) ethylamine hydrochloride in 100 cc of perfumed distilled water.

EXAMPLE 54

A lotion containing 1.8 g of 2-dodecylthio ethylamine hydrochloride in 100 cc of 50% aqueous ethyl alcohol solution.

EXAMPLE 55

A cosmetic product having the following composition is prepared:

| | |
|---|---|
| 2-cetylthio ethylamine hydrochloride | 1.25 g |
| Carboxyvinyl polymer-carboxy polymethylene, sold under the trade name "Carbopol 940" | 1.50 g |
| Triethanolamine, q.s.p. | pH 8 |
| Perfume | 0.1 g |
| Ethanol | 20 cc |
| Water, q.s.p. | 100 cc |

EXAMPLE 56

A composition according to the invention is prepared by mixing:

| | |
|---|---|
| 2-acetamido 3-benzylthio propionic acid | 2 g |
| Triethanolamine, q.s.p. | pH 7 |
| Water, q.s.p. | 100 cc |

EXAMPLE 57

A composition according to the invention is made by mixing:

| | |
|---|---|
| 2-acetamido 3-benzylthio propionic acid | 1.8 g |
| Triethanolamine, q.s.p. | pH 6 |
| 20% ethanol, q.s.p. | 100 g |

EXAMPLE 58

A composition according to the invention is prepared by mixing together:

| | |
|---|---|
| 3-Benzylthio 2-nicotinamido propionic acid | 2 g |
| Triethanolamine, q.s.p. | pH 7.4 |
| Water, q.s.p. | 100 g |

EXAMPLE 59

A composition according to the invention is made by mixing:

| | |
|---|---|
| 5-acetamido 3-thia hexanedioic acid | 2 g |
| Triethanolamine, q.s.p. | pH 7 |
| Water, q.s.p. | 100 g |

EXAMPLE 60

A cream for use on the face is prepared by mixing together:

| | |
|---|---|
| 2-benzylthio ethylammonium tartrate | 2 g |
| Cetylstearyl alcohol oxyethylenated with 15 moles ethylene oxide | 7 g |
| Silicone oil (dimethylpolysiloxane having a viscosity of 20–22 degrees at room temperature) | 1 g |
| Diethylene glycol stearate | 6 g |
| Methyl parahydroxybenzoate sold under the trade name "Nipagin M" | 0.10 g |
| n-propyl parahydroxybenzoate sold under the trade name "Nipasol" | 0.10 g |
| Water, q.s.p. | 100 cc |

EXAMPLE 61

A milk is prepared by mixing together:

| | |
|---|---|
| 2-(2-p-methoxy phenyl 2-propyl thio) ethylamine hydrochloride | 2 g |
| Carboxy vinyl polymer-carboxy polymethylene sold under the trade name "Carbopol 934" (U.S. Pat. No. 3,133,865) | 0.375 g |
| Isopropyl ester of fatty acids of lanolin | 1 g |
| Lanolin oxyethylenated with 16 moles ethylene oxide | 2.5 g |
| Cetyl stearyl alcohol oxyethylenated with 15 moles ethylene oxide | 3 g |
| Substituted alkylamide | 2 g |
| Ethyl alcohol | 20 cc |
| Triethanolamine, q.s.p. | pH 8 |
| Methyl parahydroxybenzoate sold under the trade name "Nipagin M" | 0.10 g |
| n-propyl parahydroxybenzoate sold under the trade name "Nipasol" | 0.10 g |
| Water, q.s.p. | 100 g |

EXAMPLE 62

A cream is prepared by mixing the following constituents:

| | |
|---|---|
| Cetyl alcohol | 7 g |
| Mineral or vegetable oil (Vaseline or sweet almond oil) | 5 g |
| Stearic acid | 2 g |
| Polyoxyethylenated sorbitol derivative | 16 g |
| Methyl parahydroxybenzoate sold under the trade name "Nipagin M" | 0.3 g |
| 2-(2,4-dichlorophenyl thio) ethylamine | 2 g |
| Water, q.s.p. | 100 g |

EXAMPLE 63

A cream identical to the one in Example 62 is prepared, except that the 2-(2,4-dichlorophenyl thio) ethylamine is replaced by 2-trityl thio ethylamine hydrochloride.

EXAMPLE 64

A composition identical to the one in Example 62 is prepared, except that the 2-(2,4-dichlorophenyl thio) ethylamine is replaced by 5-amino 3-thia hexanedioic acid.

EXAMPLE 65

A cream is prepared by mixing the following constituents:

| | |
|---|---|
| 2-benzyl thio ethylammonium succinate | 2 g |
| Cetyl stearyl oxyethylenated with 15 moles ethylene oxide | 7 g |
| Silicone oil (dimethyl-polysiloxane having a viscosity of 20-22 degrees at room temperature) | 1 g |
| Polyglycol stearate | 6 g |
| Parahydroxybenzoic acid ester | 0.20 g |
| Water, q.s.p. | 100 g |

EXAMPLE 66

A masking cream is prepared by mixing the following ingredients:

| | |
|---|---|
| 3,3'-(2-butene 1,4-diyl dithio) dialanine | 2 g |
| Titanium oxide | 10 g |
| Red iron oxide | 0.3 g |
| Yellow iron oxide | 0.2 g |
| Brown iron oxide | 0.4 g |
| Chestnut iron oxide | 0.2 g |
| Cetyl stearyl alcohol oxyethylenated with 15 moles ethylene oxide | 7 g |
| Silicone oil (dimethyl polysiloxane having a viscosity of 20–22 degrees at room temperature) | 1 g |
| Polyglycol stearate | 6 g |
| Para-hydrobenzoic acid ester | 0.20 g |
| Water, q.s.p. | 100 g |

EXAMPLE 67

A milk is prepared by mixing the following ingredients:

| | |
|---|---|
| Cetyl stearyl alcohol oxyethylenated with 15 moles ethylene oxide | 2.6 g |
| Antioxidant | 0.01 g |
| Cetyl alcohol | 2.6 g |
| Stearic acid | 1.6 g |
| Mineral oil (vaseline) | 6.85 g |
| Vegetable oil (sweet almond oil) | 1.3 g |
| Lanolin oxyethylenated with 16 moles ethylene oxide | 0.26 g |
| Methyl parahydroxybenzoate, sold under the trade name "Nipagin M" | 0.2 g |
| Isopropyl myristate | 4.5 g |
| Perfume (rose oil) | 0.3 g |
| 2-(2,4-dichloro benzylthio) ethylammonium 1-aspartate | 1 g |
| Water, q.s.p. | 100 g |

EXAMPLE 68

A milk identical to the one described in Example 67 is prepared, except that the 1 g of 2-(2,4-dichlorobenzylthio) ethylammonium 1-aspartate is replaced by 2 g of N-(2-phenyl thio ethyl) chloracetamide and the 1.6 g of stearic acid by 0.6 g of the same.

EXAMPLE 69

A milk identical to the one described in Example 67 is prepared, except that the N-(2-phenyl thio ethyl) chloracetamide is replaced by 2-(2,4-dichloro benzylthio) ethylammonium 1-aspartate

EXAMPLE 70

A milk is prepared by mixing together the following ingredients:

| | |
|---|---|
| 2-trityl thio ethylammonium lactate | 2 g |
| Carboxy vinyl polymer-carboxy polymethylene, sold under the trade name "Carbopol 934" | 0.375 g |
| Isopropyl esters of fatty acids of lanolin | 1 g |
| Lanolin oxyethylenated with 16 moles ethylene oxide | 2.5 g |
| Cetyl stearyl alcohol oxyethylenated with 15 moles ethylene oxide | 3 g |
| Isopropanolamine myristate | 2 g |
| Triethanolamine, q.s.p. | pH 8 |
| N—propyl parahydroxybenzoate, sold under the trade name "Nipasol" | 0.10 g |
| Water, q.s.p. | 100 g |

EXAMPLE 71

A lotion is prepared by mixing the following ingredients:

| | |
|---|---|
| 5-amino 3-thia hexanedioic acid | 0.25 g |
| Monohydrate of [diisobutylphenoxy-ethoxyethyl-dimethyl-benzyl] ammonium chloride | 0.75 g |
| Triethanolamine | 9 cc |
| Perfume | 0.05 g |
| 96° ethanol in water | 20.8 g |
| Water, q.s.p. | 100 g |

EXAMPLE 72

A lotion is prepared which is identical to the one described in Example 71 except that the cationic quaternary ammonium bactericide is replaced by hexachlorophene.

EXAMPLE 73

A foaming gel is prepared by mixing the following ingredients:

| | |
|---|---|
| Carboxyvinyl polymer-carboxy polymethylene, sold under the trade name "Carbopol 934" | 25 g |
| Magnesium ethoxy lauryl sulfate | 8 g |
| Glycerol | 10 g |
| Ammonia | 0.2 g |
| 3-carboxymethyl thio alanine | 2 g |
| Water, q.s.p. | 100 g |

EXAMPLE 74

An aerosol foam is prepared by mixing the following ingredients in an aerosol bomb:

| | |
|---|---|
| Carboxy vinyl polymer-carboxy polymethylene, sold under the trade name "Carbopol 934" | 25 g |
| Magnesium ethoxylauryl sulfate | 8 g |
| Glycerol | 10 g |
| Ammonia | 0.2 g |
| 2($\beta$-amino ethylthio) pyridine N—oxide hydrochloride | 2 g |
| Water, q.s.p. | 100 g |

88 g of the above solution are packaged in an aerosol can with 12 g of difluorodichloromethane.

2. CARRIER—LOWER ALKANOL OR AQUEOUS LOWER ALKANOL SOLUTION WITH A COSMETIC RESIN

EXAMPLE 75

A thick lacquer of the following composition is prepared:

| | |
|---|---|
| Vinyl acetate-crotonic acid copolymer sold under the trade name "Resin 28.1310" (M.W. about 20,000) | 8 g |
| 2-amino-2-methyl-1-propanol | 0.8 g |
| 2-amino 4-(o-chlorobenzylthio) methyl butyrate hydrochloride | 0.20 g |
| Perfume | 0.40 g |

| Absolute ethanol | 100 g |
|---|---|

30 grams of this solution are packaged in an aerosol can with a mixture of liquefied propellant gases containing: 42 g of trichloromonofluoromethane and 28 g of dichlorodifluoromethane.

When regularly applied on greasy hair, this lacquer gradually reduces its greasy appearance.

EXAMPLE 76

The following solution is prepared:

| Polyvinylpyrrolidone/vinyl acetate resin, sold under the trade name "E 335" K value (1% ethanol solution) = 25–35 | 10 g |
|---|---|
| N—[2-(3,5-dichlorobenzylthio) ethyl] trifluoroacetamide | 0.5 g |
| Methyl chloroform | 15 g |
| Absolute ethanol | 100 g |

To prepare a lacquer for greasy hair, 30 g of the above solution are packaged in an aerosol can also containing 49 g of trichloromonofluoromethane and 21 g of dichlorodifluoromethane. This lacquer has properties similar to that of Example 75.

EXAMPLE 77

The following solution is prepared:

| Vinyl acetate-crotonic acid copolymer, sold under the trade name "Resin 28.1310" (M.W. about 20,000) | 8 g |
|---|---|
| 2-mono-2-methyl-1-propanol | 0.8 g |
| 2-p-methoxy phenylthio ethylamine hydrobromide | 2 g |
| Cedar oil | 0.5 g |
| Absolute ethanol | 100 g |

The pH of this composition is 8.2.

To obtain a lacquer for greasy hair, 25 g of this solution are packaged in an aerosol can with 52 g of a trichloromonofluoromethane and 23 g of dichlorodifluoromethane.

A good lacquer for greasy hair is thus obtained.

EXAMPLE 78

A men's hair-dressing aerosol composition is prepared, containing:

| Polyvinylpyrrolidone-vinyl acetate copolymer, sold under the trade name "E 735" K value (1% ethanol solution) = 30–50 | 4 g |
|---|---|
| 2-benzylthio ethylammonium pantothenate | 1 g |
| Ethyl nicotinate | 0.2 g |
| Absolute ethanol | 100 g |

20 g of this solution are packaged in an aerosol can also containing under pressure 48 g of trichloromonofluoromethane and 32 g of dichlorodifluoromethane.

EXAMPLE 79

A dyeing setting lotion is prepared, designed for application on white hair of greasy appearance, of the following formula:

| Polyvinyl pyrrolidone (P.V.P.) K value = 30, M.W. 40,000 | 0.4 g |
|---|---|
| Vinylacetate crotonic acid copolymer (resin 28.1310 of National Starch) (M.W. 20,000) | 0.2 g |
| Ethanol, q.s.p. | 50° |
| 2-(3,4-methylene dioxy benzylthio) ethylamine hydrochloride | 0.7 g |
| Aminopropylamino-1 anthraquinone | 0.03 g |
| Picramic acid | 0.017 g |
| N—α-amino propylamino-4 N'—methylamino-1 anthraquinone | 0.040 g |
| Water | 100 g |

The pH value is adjusted to 7 by adding triethanolamine.

A good setting lotion is thus obtained which, when applied on white hair, gives it a smoky gray shimmer while considerably improving its initial greasy appearance.

3. CARRIER—DETERGENTS

EXAMPLE 80

A shampoo is made in accordance with the invention by mixing:

| Technical (100%) triethanolamine lauryl sulfate | 5 g |
|---|---|
| Lauryl diethanolamide | 2 g |
| 2-benzylthio ethylammonium nicotinate | 2 g |
| Carboxymethylcellulose | 0.25 g |
| Perfume | 0.2 g |
| Water, q.s.p. | 100 g |

EXAMPLE 81

A shampoo according to the invention is prepared as follows:

| Technical (100%) triethanolamine lauryl sulfate | 6 g |
|---|---|
| Lauryl diethanolamide | 2 g |
| 2-(3,4-dimethoxy benzylthio) ethylammonium malate | 2.5 g |
| Carboxymethylcellulose | 0.2 g |
| Perfume | 0.4 g |
| Water, q.s.p. | 100 g |

EXAMPLE 82

A shampoo having the following composition is prepared:

| Technical (100%) triethanolamine lauryl sulfate | 7 g |
|---|---|
| Lauryl diethanolamide | 2 g |
| 3-(2-pyridyl N—oxide methylthio) alanine | 4 g |
| Carboxymethylcellulose | 0.25 g |
| Perfume | 0.2 g |
| Water, q.s.p. | 100 g |

EXAMPLE 83

The following shampoo is prepared:

| Sodium laurylsulfate oxyethylenated with 2.2 moles of ethylene oxide | 5 g |
|---|---|

-continued

| | |
|---|---|
| Pure mono lauryl sodium sulfosuccinate | 1 g |
| Polyethylene glycol distearate | 1.5 g |
| Lauryl diethanolamide | 2.5 g |
| 2-o-chlorobenzylthio ethylammonium nicotinate | 2 g |
| Perfume | 0.2 g |
| Lactic acid, q.s.p. | pH 6.5 |
| Water, q.s.p. | 100 g |

EXAMPLE 84

| | |
|---|---|
| Sodium laurylsulfate oxyethylenated with 2.2 moles of ethylene oxide | 8 g |
| Pure mono lauryl sodium sulfosuccinate | 1.5 g |
| Polyethylene glycol distearate | 1 g |
| Lauryl diethanolamide | 2 g |
| 2-(p-methoxy benzylthio) ethyl-ammonium malate | 3 g |
| Perfume | 0.4 g |
| Lactic acid, q.s.p. | pH 6.5 |
| Water, q.s.p. | 100 g |

EXAMPLE 85

| | |
|---|---|
| Sodium laurylsulfate oxyethylenated with 2.2 moles of ethylene oxide | 6 g |
| Pure mono lauryl sodium sulfosuccinate | 1 g |
| Lauryl diethanolamide | 2.5 g |
| 2-(p-methanesulfonyl benzylthio) ethyl-amine hydrochloride | 5 g |
| Perfume | 0.3 g |
| Lactic acid q.s.p. | pH 6 |
| Water, q.s.p. | 100 g |

EXAMPLE 86

| | |
|---|---|
| Technical (100%) triethanolamine lauryl sulfate | 7 g |
| Lauryl diethanolamide | 2 g |
| 5-amino 3-thia dipropyl hexane dioate hydrochloride | 3 g |
| Carboxymethylcellulose | 0.25 g |
| Perfume | 0.4 g |
| Water, q.s.p. | 100 g |

EXAMPLE 87

| | |
|---|---|
| Sodium laurylsulfate oxyethylenated with 2.2 moles of ethylene oxide | 9 g |
| Pure mono lauryl sodium sulfosuccinate | 1 g |
| Polyethylene glycol distearate | 2 g |
| Lauryl diethanolamide | 2 g |
| 6-amino 3-thia heptane dioic acid | 2 g |
| Perfume | 0.3 g |
| Triethanolamine, q.s.p. | pH 7 |
| Water, q.s.p. | 100 g |

A composition identical to the above one is prepared except that the 5-amino 3-thia heptane dioic acid is replaced by 6-6′-sulfonyl bis(2-acetamido 4-thia hexanedioic acid), the pH being adjusted to 6.5 by adding triethanolamine.

EXAMPLE 88

A shampoo cream is prepared as follows:

| | |
|---|---|
| Sodium lauryl sulfate | 10 g |
| Product of the condensation of fatty acids of copra with the methyltaurine, a paste sold under the trade name "Hostapon C.T." | 45 g |
| Lauryl monoethanolamide | 2 g |
| Glycerol monostearate | 4 g |
| 2-phenyl thio ethylammonium Lactic acid, q.s.p. | 2 g |
| Lactic acid, q.s.p. | pH 6.6 |
| Perfume | 0.2 g |
| Water, q.s.p. | 100 g |

EXAMPLE 89

A shampoo cream in accordance with the invention is prepared as follows:

| | |
|---|---|
| Sodium lauryl sulfate | 12 g |
| Product of the condensation of fatty acids of copra with the methyltaurine, a paste sold under the trade name "Hostapon C.T." | 40 g |
| Lauryl monoethanolamide | 2 g |
| Glycerol monostearate | 4 g |
| 2-[2,2-dimethoxy ethylthio] ethylamine hydrochloride | 3 g |
| Lactic acid, q.s.p. | pH 6.5 |
| Perfume | 0.2 g |
| Water, q.s.p. | 100 g |

EXAMPLE 90

A shampoo powder in accordance with the invention is prepared as follows:

| | |
|---|---|
| Sodium lauryl sulfate powder | 50 g |
| Product of the condensation of the fatty acids of copra with the sodium isethionate sold under the trade name "Hostapon K.A." | 41 g |
| 2-(2,4-dichlorobenzylthio) ethylammonium propionate | 8 g |
| Perfume | 1 g |

EXAMPLE 91

A shampoo powder is prepared as follows:

| | |
|---|---|
| Sodium lauryl sulfate powder | 40 g |
| Product of the condensation of fatty acids of copra with the sodium isethionate sold under the trade name "Hostapon K.A." | 29 g |
| 3-octylthio alanine | 20 g |
| Perfume | 1 g |

The powder of Examples 90 and 91 can be dissolved in 10 times its weight of water and the resulting solution applied to the head.

EXAMPLE 92

A dye shampoo of the present invention is prepared as follows:

| | |
|---|---|
| 2-amino 4-thia heptanedioic acid | 5 g |
| Lauryl ammonium sulfate combined with 2 moles of ethylene oxide | 250 g |
| Copra diethanolamide | 50 g |
| Paratoluylenediamine | 10 g |
| Metadiamino anisol sulfate | 0.5 g |
| Resorcinol | 5 g |
| Metaaminophenol | 1.5 g |
| Paraminophenol | 1 g |
| Ethylene diamine tetracetic acid | 3 g |

| -continued | |
|---|---|
| 40% sodium bisulfate | 15 g |
| Water, q.s.p. | 1000 g |

This product is mixed with 1000 g of hydrogen peroxide at 20 volumes and hair containing 80% white hair is impregnated therewith. A chestnut color results.

The above shampoo compositions can have a pH range of 6.5 to 8.

Hostapon CT is a compound having the formula:

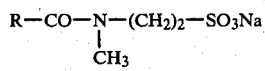

in which R is a radical derived from copra fatty acids, while Hostapon KA, is a compound having the formula:

$$R-COO-(CH_2)_2-SO_3Na$$

in which R is a radical derived from copra fatty acids.

4. CARRIER—REDUCING AND OXIDIZING AGENTS FOR PERMANENT WAVE COMPOSITIONS

EXAMPLE 93

The following reducing composition is prepared:

| Ammonium thioglycolate | 9.5 g |
|---|---|
| Fatty alcohol polyethoxy-ester | |
| (Cetyl alcohol 30% Stearyl alcohol 70%) | |
| sold under the trade name "Sipol Wax A.O." | 0.8 g |
| Ammonia, q.s.p. solution | 0.7 N |
| 5-amino 3-thia hexanedioic acid | 1.2 g |
| Water, q.s.p. | 100 g |

After shampooing and drying, the hair is wound on curlers and is impregnated with the above composition. The composition is allowed to act for 15 to 30 minutes. Thereafter, the hair is thoroughly rinsed and there is then applied to the hair a neutralizing composition comprising a 6-volume hydrogen peroxide solution. The curlers are removed and the hair is rinsed and dried. The hair thus permanently waved in accordance with this invention exhibited a nonoily appearance for a significantly longer time than did the hair when permanently waved using essentially the same cosmetic composition but without the 5-amino 3-thia hexanedioic acid.

EXAMPLE 94

The following reducing composition is prepared:

| Thioglycolic acid | 8 g |
|---|---|
| Mono-ethanolamine | 5.3 g |
| Ammonium bicarbonate | 7.7 g |
| Trimethyl-cetyl ammonium bromide | 0.2 g |
| Urea | 5.0 g |
| 3-(4-carboxy butylthio) alanine | 0.5 g |
| Water, q.s.p. | 100 g |

Proceeding as in Example 93, the above composition is applied to pre-shampooed and dried oily hair in the first stage of the permanent waving operation. Thereafter the hair is neutralized essentially as described above and a permanent wave of good quality is obtained. As before, the hair permanently waved in accordance with this invention exhibited a non-oily appearance for a significantly longer period of time than did the hair when permanently waved using essentially the same cosmetic composition but without the 3-(4-carboxy butylthio) alanine.

EXAMPLE 95

The first stage, i.e., the reducing stage, of a permanent wave operation is achieved essentially as set forth in Example 93 but with a cosmetic composition containing:

| Ammonium thioglycolate | 9.5 g |
|---|---|
| Fatty alcohol polyethoxy-ester (cetyl alcohol 30% - stearyl alcohol 70%) sold under the trade name of "Sipol Wax AO" | 0.8 g |
| Ammonia solution, q.s.p. | 0.7 N |
| Water, q.s.p. | 100 g |

Thereafter the hair, while still rolled on curlers, is neutralized by applying to the same the following neutralizing composition:

| Sodium bromate | 18 g |
|---|---|
| 3-(carboxy methylthio) alanine | 0.5 g |
| Water, q.s.p. | 100 g |

After rinsing, the curlers are removed and the hair is then dried. A good permanent wave is obtained and the hair remained non-oily in appearance for a significantly longer time than did the hair when permanently waved using a cosmetic composition essentially as described above but without any 3-(carboxy methylthio) alanine.

EXAMPLE 96

To give a permanent to hair with an oily appearance, a one stage permanent wave solution having the following composition is prepared:

| Glycol thioglycolate | 6 g |
|---|---|
| Glycol dithiodiglycolate | 18 g |
| 5-p-toluene sulfonamido 3-thia hexanedioic acid | 1 g |
| Ammonia q.s.p. | pH 9.5 |
| Water, q.s.p. | 100 cc |

After the hair has been shampooed and dried, each lock is impregnated with said solution and is then wound on curlers with a medium diameter. When the rolling has been completed, all the locks are saturated with the same solution and the head is covered with a cap. The solution is permitted to remain on the hair for a period of about 20–25 minutes. The hair is then carefully and abundantly rinsed in lukewarm water. After the curlers are removed the hair is rinsed again. The permanent wave achieved is very pronounced and supple and the hair remained non-oily in appearance for a significantly longer time than did the hair when permanently waved using essentially the same cosmetic composition but without the 5-p-toluene sulfonamido 3-thia hexanedioic acid.

EXAMPLE 97

To permanently wave hair presenting an oily appearance, a two-package reducing composition is employed.
The first package contains:

| Ammonium thioglycolate | 9.5 g |
|---|---|

| | | |
|---|---|---|
| -continued | | |
| Monoethanolamine, q.s.p. solution | 0.65 | N |
| Ammonium lauryl sulfate | 0.5 | g |
| Water, q.s.p. | 100 | g |

The second package contains:

| | |
|---|---|
| S—(β-aminopropyl) mercaptoacetic acid in powder form. | 1 g |

Immediately prior to initiating the first stage of the permanent waving operation, i.e., the reducing stage, the powdered S-(β-aminopropyl) mercapto acetic acid is dissolved in the aqueous solution constituting the first package.

The hair, wound on the curlers, is then impregnated with the resulting solution and the method outlined in Example 93 is repeated. A permanent wave is obtained which exhibits good holding characteristics and the hair remained non-oily in appearance for a significantly longer time than did the hair when permanently waved using essentially the same reducing composition but without the S-(β-aminopropyl) mercapto acetic acid.

EXAMPLE 98

The first stage, i.e., the reducing stage, of a permanent waving operation is performed with a reducing composition containing:

| | |
|---|---|
| Ammonium thioglycolate | 9.5 g |
| Fatty alcohol polyethoxy-ester (Cetyl alcohol 30% - stearyl alcohol 70%) sold under the trade name of "Sipol Wax AO" | 0.8 g |
| Ammonia solution, q.s.p. | 0.7 N |
| Water, q.s.p. | 100 g |

A two-package neutralizing composition is then employed, the first package containing:

| | | |
|---|---|---|
| Hydrogen peroxide, q.s.p. | 6.6 | volumes |
| Citric acid | 0.1 | g |
| Water, q.s.p. | 100 | g |
| and the second package containing: 3-(2-pyridyl methylthio) alanine in powder form | 5 | g |

Immediately prior to initiating the second stage of the permanent waving operation, i.e., the neutralizing stage, the powdered 3-(2-pyridyl methylthio) alanine is dissolved in the hydrogen peroxide solution and the hair previously treated with the above reducing agent, being soft and pliable and still wound on curlers, is treated with the resulting neutralizing solution for a time sufficient to reform the disulphide bonds in the keratin of the hair.

After the hair has been rinsed, unwound from the curlers, and dried, a permanent wave is obtained which exhibits good holding characteristics. Equally important, however, is that the hair remained non-oily in appearance for a significantly longer time than did the hair when permanently waved using essentially the same neutralizing composition but without the 3-(2-pyridyl methylthio) alanine.

EXAMPLE 99

The first stage, i.e., the reducing stage, to obtain a permanent wave in oily hair is performed, after shampooing the hair, with a two-package reducing composition wherein the first package contains:

| | | |
|---|---|---|
| Ammonium thioglycolate | 9.5 | g |
| Monoethanolamine q.s.p. solution | 0.65 | N |
| Ammonium lauryl sulfate | 0.5 | g |
| Water, q.s.p. | 100 | cc |
| and the second package contains: | | |
| 2-furfuryl thioethyl ammonium malate | 1 | g |

The contents of the second package are dissolved in the aqueous reducing agent of the first package. Thereafter the method outlined in Example 97 is repeated. An equally good permanent wave is obtained with comparable non-oily appearance characteristics.

EXAMPLE 100

By proceeding as indicated in Example 98, the second stage of a permanent wave operation is performed for oily hair with a two-package neutralizing composition. The first package contains:

| | | |
|---|---|---|
| Hydrogen peroxide, q.s.p. | 6.6 | volumes |
| Citric Acid | 0.1 | g |
| Water, q.s.p. | 100 | cc |
| and the second package contains: | | |
| 3-benzylthio propyl ammonium glycolate | 5 | g |

The contents of the packages are mixed just before the second stage operation is initiated. The resulting permanently waved hair exhibits non-oily appearance characteristics comparable to that achieved when the method of Example 98 was followed.

The methods outlined in Examples 93–100 are repeated using in certain instances, other compounds enumerated above, in the reducing composition, and in other instances in the neutralizing composition and in amounts essentially equivalent to those specified in Examples 93–100.

EXAMPLE 101

The following reducing composition is prepared:

| | | |
|---|---|---|
| Ammonium thioglycolate | 9.5 | g |
| Fatty alcohol polyethoxy-ester (cetyl alcohol 30% - stearyl alcohol 70%) sold under the trade name "Sipol Wax AO" | 0.8 | g |
| Ammonia q.s.p. solution | 0.7 | N |
| 2-Acetamido 3-phenylthio alanine | 2 | g |
| Water, q.s.p. | 100 | g |

After shampooing and drying, the hair is wound on curlers and is impregnated with the above composition. The composition is allowed to act for 15 to 30 minutes. Thereafter, the hair is thoroughly rinsed and there is then applied to the hair a neutralizing composition comprising a 6-volume hydrogen peroxide solution. The curlers are removed and the hair is rinsed and dried. The hair thus permanently waved in accordance with this invention exhibited a non-oily appearance for a significantly longer time than did the hair when permanently waved using essentially the same cosmetic composition but without the above active compound.

5. MISCELLANEOUS CARRIERS

EXAMPLE 102

A composition for treating the scalp to reduce excessive secretion of sebum is made by homogenizing 1.5% by weight of 3-tritylthio alanine and 0.1% of perfume in olive oil.

EXAMPLE 103

A composition according to the invention is prepared by mixing together:

| | |
|---|---|
| 3-benzylthio 2-butyramido alanine | 1.8 g |
| Olive oil, q.s.p. | 100 g |

EXAMPLE 104

A 5% by weight solution of magnesium stearate in isopropyl myristate is prepared at a temperature of 120° to 130° C. 2% by weight of 3-(3,4-methylenedioxy benzylthio) alanine is added at the same temperature, and the composition is then rapidly cooled to room temperature. A composition in accordance with the invention is thus obtained as an opaque gel.

EXAMPLE 105

A dermatological cake is prepared by mixing the following ingredients:

| | |
|---|---|
| Fatty ester of sodium isethionate "IGEPON A" R—COO—CH$_2$—CH$_2$SO$_3$Na, R being 12–18 carbon atoms | 75 g |
| Superfatting and hydrating excipient lanolin derivatives sold by CRODA under the trade name of "Super Hartolan" | 23 g |
| 3-carboxymethylthio alanine | 2 g |

EXAMPLE 106

A dermatological cake is prepared which is identical to the one described in Example 105 except that the 3-carboxymethylthio alanine is replaced by di-(2-benzylthio ethylammonium) fumarate.

EXAMPLE 107

A dermatological cake is prepared which is identical to the one described in Example 105 except that the 3-carboxymethylthio alanine is replaced by 3-benzylthio propylammonium p-aminobenzoate.

EXAMPLE 108

A dermatological cake is prepared which is identical to the one described in Example 105 except that the 3-carboxymethylthio alanine is replaced by 2-benzylthio ethylammonium pantothenate.

In the above examples, the active compound is present generally in amounts ranging from about 0.1–5 weight percent of the total composition. When the carrier is an aqueous alcohol solution, the alcohol employed generally is a lower alkanol having about 1–4 carbon atoms, the alcohol being present in amounts of about 20 to 70 weight percent of the solution. These same lower alkanols of course can be used without water when desired.

In the examples where a detergent is employed in the composition, detergents such as cationic detergents, for instance lauryldimethylbenzyl-ammonium chloride, stearyldimethylbenzyl-ammonium chloride, anionic detergents such as sodium lauryl sulphate and nonionic detergents such as sorbitan monolaurate can be used.

A typical example of a shampoo contains 7% by weight stearyldimethylbenzyl-ammonium chloride, 2% 2-propionamido 4-thia heptanedioic acid, 93% water plus a perfume and coloring agent, if desired. The shampoo is then applied to the scalp in the manner one would apply any other shampoo. That is to say the hair is rinsed with water, the shampoo is applied and rubbed into the hair and scalp, then the hair is rinsed with water to remove the shampoo. Preferably this is followed by a second shampoo washing.

Other detergents usefully employed include: anionic detergents such as: alkyl sulfates, alkyl ether sulfates, alkyl polyether sulfates, alkyl sulfonates, in which the alkyl groups have 8 to 18 carbon atoms, sulfated monoglycerides, sulfonated monoglycerides, sulfated alkanolamides, sulfonated alkanolamides, soaps of fatty acids, monosulfosuccinates of fatty alcohols, the products of the condensation of fatty acids with methyl-taurine, the products of the condensation of fatty acids with sarcosine, the products of the condensation of fatty acids with a protein hydrolysate; cationic detergents such as long chain quaternary ammonium esters of fatty acids and of amine alcohols, polyether amines, nonionic detergents such as: the esters of polyols and sugars, the products of the condensation of ethylene oxide with fatty acids, fatty alcohols, long chain alkyl phenyls, long chain mercaptans, and long chain amides, the polyethers of polyhydroxylated fatty alcohols: or amphoteric detergents such as asparagine derivatives, the products of the condensation of monochloroacetic acid and imadazolines, and alkyl aminopropionates.

Among the non-ionic detergents which can be utilized are:
lauryl alcohol oxyethylenated with 12 moles of ethylene oxide;
C$_{12}$ thiols oxyethylenated with 12 moles of ethylene oxide.

Among the cationic detergents which can be utilized are:
lauryl benzyl dimethyl ammonium bromide or chloride;
cetyl trimethyl ammonium bromide; myristil benzyl dimethyl ammonium bromide or chloride;
cetyl benzyl dimethyl ammonium bromide or chloride.

Among the amphoteric detergents which can be utilized are:
lauryl aminopropionate of a radical derived from copra fatty acids;
alkyl dimethyl betaine;
compounds of formula:

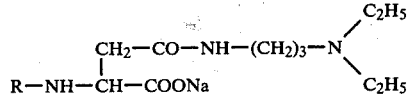

in which R is a radical derived from copra fatty acids having 6–18 carbon atoms and an alkyl derived from tallow.

The shampoos according to the invention generally contain from 0.5 to 5%, and preferably 1 to 3% by weight of the said active compound. They also contain, for example, from 4 to 15%, and preferably from 5 to 7% by weight of the detergent compound in an aqueous medium.

The shampoos according to the invention may also contain other conventional cosmetic ingredients, such as perfumes and hair dyes. They can also contain thickening agents such as the alkanolamides of fatty acids, cellulose derivatives (carboxymethylcellulose, and hydroxymethylcellulose, for example), esters of long chain polyols, and natural gums so as to take the form of a cream or gel.

The shampoos according to the invention may also take the form of a powder adapted to be applied to moistened hair, or to be dissolved in a certain volume of water before being used to wash the hair.

When the novel compositions of this invention include a cosmetic resin in combination with the active compound to provide a hair setting lotion or lacquer, useable cosmetic resins employed include, for instance, polyvinylpyrrolidone (M.W. 40,000) and generally between 10,000–70,000; polyvinylpyrrolidone/vinyl acetate copolymer 70%:30% to 30%:70% (K ethanol 1% 25–50); copolymer of vinyl acetate and an unsaturated carboxylic acid such as crotonic acid (M.W. 20,000); copolymer resulting from the polymerization of vinyl acetate (75–85%), crotonic acid 5–15% and an acrylic or methacrylic ester (5–15%), copolymer resulting from the copolymerization of vinyl acetate (75–85%), crotonic acid (5–15%) and vinyl alkyl ether (5–15%); copolymer resulting from the copolymerization of vinyl acetate (63–88%), crotonic acid (5–15%) and (a) a vinyl ester of a long carbon-chain acid having 10 to 22 carbon atoms or (b) an allyl or methallyl ester of a long carbon-chain acid having 10 to 22 carbon atoms (5–25%); copolymers resulting from the copolymerization of an ester derived from an unsaturated alcohol having 2 to 12 carbon atoms and a short chain carboxylic acid having 2 to 5 carbon atoms (65–80%) and a short carbon-chain unsaturated acid having 4 to 20 carbon atoms (7–12%) and at least one ester derived from a short chain saturated alcohol having 8 to 18 carbon atoms and an unsaturated acid having 4 to 20 carbon atoms (10–20%). The resin concentration generally ranges between about 1–20% by weight of the composition.

In a particular mode of operation, the cosmetic resins contained in the compositions according to the invention may present lateral or branch chains, at the end of which a thiol function is located.

The cosmetic resins contained in the compositions according to the invention may also consist of colored polymers, i.e., polymers containing in their macromolecular chain coloring nuclei which give a particular coloration or shade to the hair.

As indicated above, the novel compositions of this invention are employed as oxidizing or reducing agents in processes for permanently waving hair.

In one embodiment, the hair is permanently waved by applying to the hair wound on curlers during the first stage, i.e., during the reducing stage, a cosmetic composition comprising a mixture of a reducing agent and the active compound of this invention, defined above, permitting the composition to remain on the hair for a time sufficient to alter the disulphide bonds of the keratin of the hair, generally about 10 to 40 minutes, thoroughly rinsing the hair to remove residual reducing agent and applying in the second stage, i.e., during the neutralization stage, an oxidizing or neutralizing agent to reform the disulphide bonds of the keratin of the hair.

In another embodiment, the hair is permanently waved by applying to the hair wound on curlers during the first stage, i.e., during the reducing stage, a reducing agent, permitting the composition to remain on the hair for a time sufficient to alter the disulphide bonds of the keratin of the hair, generally about 10 to 40 minutes, thoroughly rinsing the hair to remove residual reducing agent and applying in the second stage, i.e., during the neutralization stage, a cosmetic composition comprising a mixture of an oxidizing or neutralizing agent and the active compound of this invention whereby the disulphide bonds of the keratin of the hair are reformed.

In yet another embodiment the hair is permanently waved by impregnating the hair wound on curlers with a cosmetic composition comprising a mixture of a thiol reducing agent for altering the disulphide bonds of the keratin of the hair, an organic disulphide and the active compound as hereinbefore defined, the molar ratio of said organic disulphide to said thiol being greater than 1, and as high as about 20, permitting the composition to remain on the hair for a time sufficient to induce a permanent wave therein, generally about 10 to 40 minutes, and unwinding the hair from the curlers. Conventional separate neutralization operations are not required in the practice of this embodiment of the invention.

The aforementioned active compounds used in these embodiments are admixed with a conventional reducing agent and are present in the resulting mixture in amounts between 0.1%–5% by weight of the total and preferably between 1 and 3 weight percent. The pH of this cosmetic composition is preferably between 3 and 9.5. Conventional reducing agents employed are advantageously those organic thiols which are generally used to perform the first stage of a permanent waving operation. Representative thiols include thioglycolic acid, ammonium thioglycolate, thioglycerol, thiolactic acid, thioglycolic amide or hydrazide or the like.

Conveniently, and also in accordance with the present invention, the reducing composition is a two-package composition, the first package containing a thiol reducing agent as described above and the second package containing said active compound in amounts such that when the contents of two packages are mixed together, preferably just before initiation of the reducing operation, the resulting reducing composition contains said active compound in amounts of about 0.1–5 weight percent of the total mixture.

Alternatively, the active compound is admixed with a conventional neutralizing or oxidizing agent and is present in the resulting mixture in amounts between 0.1 and 5 weight percent, and preferably between about 1 and 3 weight percent of the total. Conventional neutralizing agents employed include, for instance, hydrogen peroxide, sodium or potassium bromate, sodium perborate or percarbonate and the like.

Conveniently also, the neutralizing composition is a two-package composition, the first package containing the neutralizing agent as described above and the second package containing the acitve compound in amounts such that when the contents of the two packages are mixed together, preferably just before initiation of the neutralizing operation, the resulting neutralizing composition contains the active compound in amounts of about 0.1–5 weight percent of the total mixture.

As a further alternative, the active compound is admixed with a single stage permanent hair waving agent, and is present in the resulting mixture in amounts between 0.1–5 weight percent, and preferably, between about 1 and 3 weight percent of the total. Conventional single stage permanent hair waving agents can be employed and include a mixture of an organic disulfide and a thiol, the mol ratio of the disulfide to the thiol being greater than 1.

Suitable thiols include thioglycolic acid, glycol thioglycolate, glycerol thioglycolate, β-mercaptoethanol, N-carboxymethyl-mercaptoacetamide, glycol thiolactate and the like.

As the organic disulphides there can be used the disulphides of the thiols set forth in the preceding paragraph. For instance, glycol dithiodiglycolate, glycerol dithiodiglycolate, glycol dithiodilactate, dithiodiethanol and N-carboxymethyldithioacetamide can be employed. Additional ingredients can include ammonia, water, urea and lower alkanols in conventionally employed amounts and the pH of the single stage permanent hair waving agent ranges between about 8–10, preferably about 8.5–9.5. Typical formulations of such single stage permanent hair waving agents are disclosed in French Pat. Nos. 1,443,888 and 1,455,788.

Again, conveniently, the single stage permanent hair waving composition is a two-package composition, the first package containing the single stage permanent hair waving agent and the second package containing the active compound of this invention as defined above, in amounts such that when the contents of the two packages are mixed together, preferably just before use, the resulting permanent hair waving composition contains the active compound in amounts of about 0.1–5 weight percent of the total mixture.

C. New Active Compounds Employed in the Composition and Method of This Invention While a significant number of the thioethers described herein and employed as the active compound in the composition and method of this invention are already known to the art, nonetheless, the present invention also provides some new thioethers which functon in the same manner.

In Table I below are listed novel cysteine derivatives, the method by which they can be prepared referring to section A herein, as well as representative compositions in which they are included for topical application to humans having a scalp or skin characterized by excessive secretion of sebum, to reduce said excessive secretion so as to improve the condition thereof.

TABLE I

| NO. | Active Compound | Method of Preparation | Form of Composition | Amount in Composition |
|---|---|---|---|---|
| 1 | 3-(2-ethyl hexylthio)alanine | I | Grooming lotion as in Ex. 39–14 42 | .75 g |
| 2 | 3-dodecylthio alanine | I | Grooming lotion as in Ex. 39–42 | 1.00 g |
| 3 | 3-hexadecylthio alanine | I | Grooming lotion as in Ex. 39–42 | 1.00 g |
| 4 | 3-octadecylthio alanine | I | Grooming lotion as in Ex. 39–42 | 2.00 g |
| 5 | 3-(9-octadecene-ylthio)alanine | I | Grooming lotion as in Ex. 39–42 | 2.00 g |
| 6 | 3,3'-(2-butene 1,4-diyl-dithio)dialanine | I | Grooming lotion as in Ex. 39–42 | 3.00 g |
| 7 | 3-(2,3-dihydroxy propylthio)alanine | IV (Alternative) | Dermal Milk as in Ex. 43–44 | 0.1 g |
| 8 | 3-(2,2-dimethoxy ethylthio)alanine | I | Dermal Milk as in Ex. 43–44 | 0.1 g |
| 9 | 3-(3,3-diethoxy propylthio)alanine | I or II | Dermal Milk as in Ex. 43–44 | 0.5 g |
| 10 | 3-(1,2-propylenedioxy ethylthio)alanine | I | Dermal Milk as in Ex. 43–44 | 0.5 g |
| 11 | 3-(2,2-ethylenedioxy propylthio)alanine | I or II | Dermal Milk as in Ex. 43–44 | 0.75 g |
| 12 | 3-(β-ureidoethylthio)alanine | I | Dermal Milk as in Ex. 43–44 | 1.0 g |
| 13 | 3-(β-phenylacetamidoethylthio)alanine | I | Dermal Milk as in Ex. 43–44 | 2.0 g |
| 14 | 3-(β-nicotinamidoethylthio)alanine | I or IV | Lotion as in Ex. 45–54 | 0.1 g |
| 15 | 3-[2-(2,4-dihydroxy 3,3-dimethyl butyramido)ethylthio] alanine | VII | " | 0.5 g |
| 16 | 3-[9,11-dihydroxy 10,10-dimethyl 4,8-dioxo 3,7-diaza undecylthio] alanine | IV | " | 0.75 g |
| 17 | S,S'-[2,3-dihydroxy 1,4-butanediyl] bis cysteine | I | " | 0.75 g |
| 18 | 3-(2-thenylthio)alanine | I | " | 1.0 g |
| 19 | 3-furfurylthio alanine | I | " | 1.5 g |
| 20 | 3-tetrahydrofurfurylthio alanine | I | " | 1.5 g |
| 21 | 3-(2-pyridyl methylthio)alanine | I | " | 2.0 g |
| 22 | 3-(2-pyridylthio)alanine | I | " | 3.0 g |
| 23 | 3-(2-pyridyl ethylthio)alanine | II or I | " | 5.0 g |
| 24 | 3-(o-methoxybenzylthio)alanine | I | Cream or Milk as in Ex. 60–66 | 1 g |
| 25 | 3-(p-butoxybenzylthio)alanine | I | Cream or Milk as in Ex. 60–66 | 1 g |
| 26 | 3-(m-fluorobenzylthio)alanine | I | Cream or Milk as in Ex. 60–66 | 1 g |
| 27 | 3-(p-fluorobenzylthio)alanine | I | Cream or Milk as in Ex. 60–66 | 1 g |
| 28 | 3-(o-fluorobenzylthio)alanine | I | Cream or Milk as in Ex. 60–66 | 2 g |
| 29 | 3-(4-isopropyl benzylthio)alanine | I | Cream or Milk as in | 2 g |

TABLE I-continued

| NO. | Active Compound | Method of Preparation | Form of Composition | Amount in Composition |
|---|---|---|---|---|
| 30 | 3-benzylthio 2-nicotinamido propionate of 2-hydroxy 2-propyl | V or VII | Cream or Milk as in Ex. 60–66 | 2 g |
| 31 | 3-benzylthio nicotinamido propionic | VII | Cream or Milk as in Ex. 60–66 | 2.5 g |
| 32 | 5-p-toluene sulfonamido 3-thia hexanedioic acid | VII | Cream or Milk as in Ex. 60–66 | 3.0 g |
| 33 | 5-p-acetamidobenzene sulfonamido 3-thia hexanedioic acid | VII | Cream or Milk as in Ex. 60–66 | 3.0 g |
| 34 | 2-propionamido 3-thia hexanedioic acid | VII | Lacquer as in Ex. 75–77 | 0.1 g |
| 35 | 2-p-acetamidobenzamido 3-benzylthio propionic acid | VII | Lacquer as in Ex. 75–77 | 0.1 g |
| 36 | 2-methanesulfonamido 3-dodecylthio propionic acid | VII | Lacquer as in Ex. 75–77 | 0.1 g |
| 37 | 5-benzamido 3-thia hexanedioic acid | VII | Lacquer as in Ex. 75–77 | 0.2 g |
| 38 | 2-glutamino 3-methylthio propionic acid | VII | Lacquer as in Ex. 75–77 | 0.2 g |
| 39 | 5-ureido 3-thia hexanedioic acid | VIII | Lacquer as in Ex. 75–77 | 0.5 g |
| 40 | N—(2-amino 3-benzylthio propionyl) glucosamine hydrochloride | VI | Lacquer as in Ex. 75–77 | 0.5 g |
| 41 | 2-formamido 4-thia heptanedioic acid | VII | Lacquer as in Ex. 75–77 | 0.5 g |
| 42 | 3-benzylthio 2-(9-octadecene amido) propionic acid | VII | Shampoo as in Ex. 80–84 | 0.5 g |
| 43 | 2-propionamido 3-benzylthio propion-hydroxamic acid | VI | Shampoo as in Ex. 80–84 | 2.0 g |
| 44 | N—(2-acetamido 3-benzylthio propionyl)glucosamine | VI | Shampoo as in Ex. 80–84 | 2.0 g |
| 45 | 2-acetamido 3-benzylthio propionate of diethylaminoethyl | V | Shampoo as in Ex. 80–84 | 2.5 g |
| 46 | 3-benzylthio 2-propionamido propionate of 1-butoxy 2-propanol | V | Shampoo as in Ex. 80–84 | 3.0 g |
| 47 | 5-amino 3-thia hexanedioate of di-($\beta$-piperidinoethyl)hydrochloride | V | Shampoo as in Ex. 80–84 | 3.5 g |
| 48 | 3,3'-(2,2'-sulfonyl diethylthio)dialanine | II | Shampoo as in Ex. 80–84 | 4.0 g |
| 49 | 3-($\beta$-piperidinocarbonyl ethylthio) alanine | I or II | Shampoo as in Ex. 80–84 | 5.0 g |
| 50 | 2-acetamido 3-pyrrolidinocarbonyl-methylthio propionic acid | I | Permanent wave Composition as in Ex. 93–95 | 1.5 g |
| 51 | 2-amino 4-ortho-chlorobenzylthio butyrate of methyl hydrochloride | I | Permanent wave Composition as in Ex. 93–95 | 1.5 g |
| 52 | 2-propionamido 4-tetradecylthio butyric acid | VII | Permanent wave Composition as in Ex. 93–95 | 1.5 g |
| 53 | S,S'—(2-butene, 1,4-diyl)bis-homocysteine | I | Permanent wave Composition as in Ex. 93–95 | 2.0 g |
| 54 | 3-propioxycarbonylmethylthio alanine | V | Lotion as in Examples 27–28 | 0.75 g |
| 55 | 3-($\omega$-methoxycarbonyl butylthio)alanine | I | Lotion as in Examples 27–28 | 1.00 g |
| 56 | 3-($\omega$-methoxycarbonyl penthylthio) alanine | I | Lotion as in Examples 27–28 | 1.00 g |
| 57 | S—carboxymethyl cysteinate of methyl | I | Lotion as in Examples 27–28 | 2.00 g |
| 58 | 5-nicotinamido 3-thia hexanedioic acid | VII | Lotion as in Examples 27–28 | 2.00 g |
| 59 | 5-p-acetamidobenzamido 3-thia hexanedioic acid | VII | Lotion as in Examples 27–28 | 3.00 g |
| 60 | 5-p-butoxybenzamido 3-thia | VII | Lotion as in Examples 27–28 | 0.75 g |
| 61 | 5-p-methoxybenzamido 3-thia hexanedioic acid | VII | Lotion as in Examples 27–28 | 1.00 g |
| 62 | 2-acetamido 4-thia nonanedioic acid | VII | Lotion as in Examples 27–28 | 1.00 g |
| 63 | 3-benzylthio 2-butyramido propionic acid | VII | Lotion as in Examples 27–28 | 2.00 g |
| 64 | 3-benzylthio 2-propionamido propionic acid | VII | Grooming lotion as in ex. 39–42 | 0.75 g |
| 65 | 3-benzylthio 2-methanesulfonamido propionic acid | VII | Grooming lotion as in ex. 39–42 | 0.75 g |
| 66 | 3-benzylthio 2-ethanesulfonamido propionic acid | VII | Grooming lotion as in ex. 39–42 | 1.00 g |

TABLE I-continued

| NO. | Active Compound | Method of Preparation | Form of Composition | Amount in Composition |
|---|---|---|---|---|
| 67 | 3-benzylthio 2-propane sulfonamido propionic acid | VII | Grooming lotion as in ex. 39–42 | 1.00 g |
| 68 | 3-benzylthio 2-butanesulfonamido propionic acid | VII | Grooming lotion as in ex. 39–42 | 2.00 g |
| 69 | 2-acetamido 3-benzylthio propionic acid | VII | Grooming lotion as in ex. 39–42 | 2.00 g |
| 70 | S—(carboxymethyl)cysteinate of butyl | I | Grooming lotion as in ex. 39–42 | 3.00 g |
| 71 | S—(ethoxy carbonyl methyl)cysteine | I and V | Grooming lotion as in ex. 39–42 | 0.75 g |
| 72 | S—(propoxy carbonyl methyl)cysteine | I and V | Grooming lotion as in ex. 39–42 | 1.00 g |
| 73 | S—(butoxy carbonyl methyl)cysteine | I and V | Grooming lotion as in ex. 39–42 | 1.00 g |
| 74 | S—(methoxy carbonyl/propyl)cysteine | I and V | Grooming lotion as in ex. 39–42 | 2.00 g |
| 75 | S—(methoxy carbonyl methyl)cysteine | I | Grooming lotion as in ex. 39–42 | 2.00 g |
| 76 | 5-amino 3-thia dimethyl hexanedioate hydrobromide | V | Grooming lotion as in ex. 39–42 | 3.00 g |

All the preceding compounds except compound 2 are new
The following compounds are known compounds.

| NO. | Active Compound | Method of Preparation | Form of Composition | Amount in Composition |
|---|---|---|---|---|
| 77 | 3-methylthio alanine | I | Dermal Milk as in Ex. 43–44 | 0.1 g |
| 78 | 3-methylthio alanine hydrochloride | I | Dermal Milk as in Ex. 43–44 | 0.5 g |
| 79 | 3-isopropylthio alanine | I or III | Dermal Milk as in Ex. 43–44 | 0.5 g |
| 80 | 3-n-octylthio alanine | I | Dermal Milk as in Ex. 43–44 | 0.75 g |
| 81 | 3-allylthio alanine | I | Dermal Milk as in Ex. 43–44 | 0.75 g |
| 82 | 3-allylthio alanine hydrochloride | I | Dermal Milk as in Ex. 43–44 | 0.75 g |
| 83 | 3-(2-butene-ylthio)alanine | I | Dermal Milk as in Ex. 43–44 | 0.75 g |
| 84 | 1,2-dichloro 3-vinylthio alanine | I | Dermal Milk as in Ex. 43–44 | 1 g |
| 85 | 3-(2-propyne-ylthio)alanine | I | Dermal Milk as in Ex. 43–44 | 2.0 g |
| 86 | 3-t-butylthio alanine | III | Dermal Milk as in Ex. 43–44 | 2.0 g |
| 87 | 3-β-hydroxyethylthio alanine | I or IV (alternative) | Dermal Milk as in Ex. 43–44 | 2.0 g |
| 88 | 3-(2-hydroxy propylthio)alanine | IV (alternative) | Dermal Milk as in Ex. 43–44 | 2.0 g |
| 89 | 3-β-acetamidoethylthio alanine | I or IV | Lotion as in Ex. 45–54 | 0.1 g |
| 90 | 2-β-p-toluenesulfonamido 3-ethylthio alanine | I or IV | " | 0.1 g |
| 91 | 3-β-aminoethylthio alanine | I or IV | " | 0.5 g |
| 92 | 3,3'-thio dialanine | II | " | 0.5 g |
| 93 | 3-(ω-amino ω-carboxypropylthio)alanine | I or II | " | 0.75 g |
| 94 | S—(3-alanyl) N—acetyl cysteine | II | " | 0.75 g |
| 95 | 3-(2-naphthyl thio)alanine | I or II | " | 1.0 g |
| 96 | 3-o-chlorobenzylthio alanine | I | " | 1.0 g |
| 97 | 3-p-chlorobenzylthio alanine | I | " | 1.5 g |
| 98 | 3-β-phenylethylthio alanine | I or II | " | 1.5 g |
| 99 | 3-diphenylmethylthio alanine | III (and I) | " | 1.5 g |
| 100 | 3-(2,4-dichloro benzylthio)alanine | I | " | 2.0 g |
| 101 | 3-(3,4-dichloro benzylthio)alanine | I | " | 2.0 g |
| 102 | 3-(3,5-dichloro benzylthio)alanine | I | " | 2.0 g |
| 103 | 3-(2,6-dichloro benzylthio)alanine | I | " | 3.0 g |
| 104 | 3-p-methoxybenzylthio alanine | I | " | 3.0 g |
| 105 | 3-p-bromobenzylthio alanine | I | " | 3.5 g |
| 106 | 3-(3,4-dimethoxy benzylthio)alanine | I | " | 5 g |
| 107 | 3-(3,4-methylenedioxy benzylthio)alanine | I | Cream or Milk as in Ex. 60–66 | 1.0 g |
| 108 | 3-(3,4,5-trimethoxy benzylthio)alanine | I | Cream or Milk as in Ex. 60–66 | 1.0 g |
| 109 | 3-(2-pyridyl N—oxide methylthio)alanine | I | Cream or Milk as in Ex. 60–66 | 1.0 g |
| 110 | 3-o-methylbenzylthio alanine | I | Cream or Milk as in Ex. 60–66 | 1.0 g |
| 111 | 3-p-methylbenzylthio alanine | I | Cream or Milk as in Ex. 60–66 | 2.0 g |
| 112 | 3-(4-t-butyl benzylthio)alanine | I | Cream or Milk as in Ex. 60–66 | 2.0 g |
| 113 | 3-(2,4-dimethyl benzylthio)alanine | I | Cream or Milk as in Ex. 60–66 | 2.0 g |

TABLE I-continued

| NO. | Active Compound | Method of Preparation | Form of Composition | Amount in Composition |
|---|---|---|---|---|
| 114 | 3-p-trifluoromethyl benzylthio alanine | I | Cream or Milk as in Ex. 60–66 | 2.5 g |
| 115 | 3-o-trifluoromethyl benzylthio alanine | I | Cream or Milk as in Ex. 60–66 | 2.5 g |
| 116 | 3-p-acetamidobenzylthio alanine | I | Cream or Milk as in Ex. 60–66 | 3.0 g |
| 117 | 3-p-dimethylamino-benzylthio alanine | I | Cream or Milk as in Ex. 60–66 | 3.5 g |
| 118 | 3-p-phenoxybenzylthio alanine | I | Cream or Milk as in Ex. 60–66 | 3.5 g |
| 119 | 3-p-phenylbenzylthio alanine | I | Cream or Milk as in Ex. 60–66 | 3.5 g |
| 120 | 3-(4-methylthio benzylthio)alanine | I | Lacquer as in Ex. 75–77 | 0.1 g |
| 121 | 3-(4-propylsulfinyl benzylthio)alanine | I | Lacquer as in Ex. 75–77 | 0.1 g |
| 122 | 3-(4-butylsulfonyl benzylthio)alanine | I | Lacquer as in Ex. 75–77 | 0.1 g |
| 123 | 3-(2-methylthio benzylthio)alanine | I | Lacquer as in Ex. 75–77 | 0.2 g |
| 124 | 3-benzylthio alanine | I | Lacquer as in Ex. 75–77 | 0.2 g |
| 125 | 2-amino 3-benzylthio propionamide hydrochloride | VI | Lacquer as in Ex. 75–77 | 0.5 g |
| 126 | 3-ethoxycarbonyl methylthio alaninate of ethyl | V | Lacquer as in Ex. 75–77 | 0.5 g |
| 127 | 2-amino 3-benzylthio propionhydroxamic acid | VI | Laquer as in Ex. 75–77 | 0.5 g |
| 128 | 2-acetamido 3-benzylthio propionhydrazide | VI | Lacquer as in Ex. 75–77 | 0.5 g |
| 129 | 3-p-ethoxy benzylthio alanine | I | Lacquer as in Ex. 75–77 | 0.5 g |
| 130 | 3-[bis-(p-methoxyphenyl)β-methylthio] alanine | I or III | Shampooing as in Ex. 80–84 | 0.5 g |
| 131 | 3-(2-p-methoxyphenyl 2-propyl thio) alanine | I or III | Shampooing as in Ex. 80–84 | 0.5 g |
| 132 | 3-(2-naphthyl methylthio)alanine | I | Shampooing as in Ex. 80–84 | 0.8 g |
| 133 | 3-phenylthio alanine | I (alternative) or II | Shampooing as in Ex. 80–84 | 0.8 g |
| 134 | 3-o, m or p-chlorophenylthio alanine | I (alternative) or II | Shampooing as in Ex. 80–84 | 1.0 g |
| 135 | 3-p-fluorophenylthio alanine | I (alternative) or II | Shampooing as in Ex. 80–84 | 2.0 g |
| 136 | 3-o or p-methoxyphenylthio alanine | I (alternative) or II | Shampooing as in Ex. 80–84 | 2.0 g |
| 137 | 3-benzylthio valine | II | Shampooing as in Ex. 80–84 | 2.0 g |
| 138 | 2-amino 4-benzylthio butyric acid | I | Shampooing as in Ex. 80–84 | 2.0 g |
| 139 | 3-carbamyl methylthio alanine | I | Shampooing as in Ex. 80–84 | 2.0 g |
| 140 | 3-γ-aminopropylthio alanine | I | Shampooing as in Ex. 80–84 | 2.5 g |
| 141 | 3-o-aminophenylthio alanine | I | Shampooing as in Ex. 80–84 | 3 g |
| 142 | 3-(2-carboxy ethylthio)alanine | II or I | Shampooing as in Ex. 80–84 | 3.5 g |
| 143 | 3-β-butoxy carbonyl ethylthio alanine | II | Shampooing as in Ex. 80–84 | 3.5 g |
| 144 | 3-propoxy carbonylmethylthio alanine | V | Shampooing as in Ex. 80–84 | 4.0 g |
| 145 | 3-ω-methoxycarbonyl butylthio alanine | I | permanent wave composition as in Ex. 93–95 | 1.5 g |
| 146 | 3-ω-methoxy carbonyl pentylthio alanine | I | permanent wave composition as in Ex. 93–95 | 1.5 g |
| 147 | 3-(3-carboxy propylthio)alanine | I | permanent wave composition as in Ex. 93–95 | 1.5 g |
| 148 | 2-amino 4-thia nonanedioic acid | II | permanent wave composition as in Ex. 93–95 | 1.5 g |
| 149 | 2-amino 4-thia decanedioic acid | I | permanent wave composition as in | 1.5 g |

TABLE I-continued

| NO. | Active Compound | Method of Preparation | Form of Composition | Amount in Composition |
|---|---|---|---|---|
| 150 | 2-amino 4-thia dodecanedioic acid | I | permanent wave composition as in Ex. 93-95 | 1.5 g |
| 151 | 3-carboxymethylthio alanine | I | permanent wave composition as in Ex. 93-95 | 1.5 g |
| 152 | 3-benzylthio 2-(10-undecene-amido) propionic acid | VII | permanent wave composition as in Ex. 93-95 | 2.0 g |
| 153 | 3-benzylthio 2-octadecanamido propionic acid | VII | permanent wave composition as in Ex. 93-95 | 2.0 g |
| 154 | 3-carbamylthio alanine | VIII | permanent wave composition as in Ex. 93-95 | 2.0 g |
| 155 | 3-methylthio 2-propionamido propionate of dimethylaminoethyl | V | Grooming lotion as in Ex. 39-42 | 0.75 g |
| 156 | 3-o-nitrophenylthio alanine | I | Grooming lotion as in Ex. 39-42 | 0.75 g |
| 157 | 2-amino 4-$\beta$-amino ethylthio butyric acid hydrochloride | I | Grooming lotion as in Ex. 39-42 | 1.0 g |
| 158 | 2-amino 4-tetradecylthio butyric acid | I | Grooming lotion as in Ex. 39-42 | 1.0 g |
| 159 | 6-amino 3-thia heptanedioic acid | I | Grooming lotion as in Ex. 39-42 | 2.0 g |
| 160 | 2-acetamido 4-thia heptanedioic acid | II or I | Grooming lotion as in Ex. 39-42 | 2.0 g |
| 161 | 5-dodecanamido 3-thia hexanedioic acid | VII | Grooming lotion as in Ex. 39-42 | 2.5 g |
| 162 | 6-amino 3-thia heptanedioate of dimethyl | V | Grooming lotion as in Ex. 39-42 | 3.0 g |
| 163 | 2-amino 3-benzhydryl propionate of methyl hydrochloride | V | Grooming lotion as in Ex. 39-42 | 3.0 g |
| 164 | Hydrochloride of 5-amino 3-thia hexanedioic acid | VII | Grooming lotion as in Ex. 39-42 | 0.75 g |
| 165 | S—(methoxy carbonyl ethyl) cysteine | II | Grooming lotion as in Ex. 39-42 | 0.75 g |
| 166 | S—(methoxy carbonyl butyl) cysteine | I and V | Grooming lotion as in Ex. 39-42 | 1.0 g |
| 167 | 3-(1-naphtyl 2-methylthio)alanine | I | Grooming lotion as in Ex. 39-42 | 1.0 g |
| 168 | 3-(triphenylmethylthio)alanine | III (and I) | Grooming lotion as in Ex. 39-42 | 2.0 g |

Table II, below, lists active compounds which are cysteamine derivatives and which are usefully employed in the present invention. Table II identifies the general method by which the active compounds are prepared in accordance with Methods I–VIII disclosed hereinbefore, as well as representative compositions in which they are included for topical application to humans having a scalp or skin characterized by excessive secretion of sebum to reduce said excessive secretion so as to improve the condition thereof.

TABLE II

| No. | Active Compound | Method of Preparation | Form of Composition | Amount in Composition |
|---|---|---|---|---|
| 1 | 2-methylthio ethylamine cinnamate | I or IV | Grooming Lotion as in Ex. 39-42 | 0.1 g |
| 2 | 2-methyl thio ethylurea | I or VIII | " | 0.1 g |
| 3 | N—(2 methylthio ethyl) p-acetamido benzamide | VII, IV or I | " | 0.1 g |
| 4 | N—(2-methylthio ethyl)p-acetamido benzenesulfonamide | VII, IV or I | " | 0.2 g |
| 5 | N—(2-propylthioethyl)-p-methoxy benzamide | VII, IV or I | " | 0.2 g |
| 6 | N—(butylthio ethyl) nicotinamide | I or VII | " | 0.5 g |
| 7 | N—(2-dodecylthio ethyl) p-butoxybenzamide | VII or IV | " | 0.5 g |
| 8 | N—(2-methylthio ethyl) p-toluenesulfonamide | VII or IV | " | 0.75 g |
| 9 | N—(2-isopropylthio ethyl) propionamide | VII or IV | " | 1.0 g |
| 10 | N—(2-octylthio ethyl) acetamide | VII or IV | " | 2.0 g |
| 11 | N—(2-butylthio ethyl) methanesulfonamide | VII or IV | Dermal Milk as in Ex. 43-44 | 0.1 g |
| 12 | N—(2-isopentylthio ethyl)butane sulfonamide | VII or IV | " | 0.2 g |
| 13 | bis 1,4-(2-acetamido ethylthio) 2,3-butanediol | I or IV | " | 0.5 g |
| 14 | 2-hexadecylthio ethylamine hydrochloride | I or IV | " | 1.0 g |
| 15 | 9-octadecene 2-ylthio ethylamine hydrochloride | I | " | 1.0 g |
| 16 | 2-allylthio ethylamine malate | I | " | 1.0 g |
| 17 | 9-octadecene 2-ylthio ethylamine | I | " | 1.0 g |

TABLE II-continued

| No. | Active Compound | Method of Preparation | Form of Composition | Amount in Composition |
|---|---|---|---|---|
|  | hydrochloride |  |  |  |
| 18 | 2-dodecylthio ethylamine hydrochloride | I or IV | " | 1.0 g |
| 19 | 2-isopentylthio ethylamine mandelate | I or IV | " | 2.0 g |
| 20 | 2-octadecylthio ethylamine salicylate | I or IV | " | 5.0 g |
| 21 | 2-($\beta$-hydroxyethyl thio) ethylurea | I or VIII | " | 5.0 g |
| 22 | 2-($\beta$-hydroxyethylthio) ethylamine hydochloride | I or IV | Lotion as in Ex. 45–54 | 0.1 g |
| 23 | 2-(2,3-dihydroxy propylthio)ethylamine p-toluenesulfonate | I or IV | " | 0.1 g |
| 24 | 2-(2-hydroxy propylthio)ethylamine oxalate | IV | " | 0.3 g |
| 25 | N—(2-methylthio ethyl)phenylacetamide | VII | " | 0.3 g |
| 26 | 2-(2,2-dimethoxy ethylthio) ethylamine hydrochloride | I | " | 0.5 g |
| 27 | 2-(2,2-dimethoxy ethylthio) ethylamine undecylenate | I | " | 0.5 g |
| 28 | 2-(2,2-diethoxy ethylthio) ethylamine undecylenate | I | " | 1.0 g |
| 29 | 2-(2,2-diethoxy ethylthio)ethylamine acetate | I | " | 1.0 g |
| 30 | 2-undecenylthio ethylamine | I | " | 2.0 g |
| 31 | 2-($\beta$-ureidoethylthio) ethylamine hydrochloride | I or IV | " | 2.5 g |
| 32 | 2-($\beta$-acetamidoethylthio) ethylamine tropate | I or IV | " | 2.5 g |
| 33 | 2,2'-thio diethylamine fumarate | I or IV | " | 4.0 g |
| 34 | 2,2'-thio diethylurea | VIII or I | " | 4.0 g |
| 35 | 3-($\beta$-aminoethylthio) propylamine hydrochloride | I or IV | " | 5.0 g |
| 36 | 2-ethoxycarbonylthio ethylamine hydrochloride | I | Cream or Milk as Ex. 60–66 | 0.5 g |
| 37 | 2-dimethylamino carbonylthio ethylamine sulfate | I | " | 0.5 g |
| 38 | 2-butoxycarbonyl methylthio ethylurea | I or V | " | 0.5 g |
| 39 | 2-ethyloxycarbonylmethylthio ethylamine hydrochloride | V | " | 0.5 g |
| 40 | 6-($\beta$-aminoethylthio)hexanoate of methyl hydrochloride | I | " | 0.75 g |
| 41 | 2-phenylthio ethylamine dihydrogen phosphate | I or IV | " | 0.75 g |
| 42 | 2-p-t-butylphenylthio ethylamine trichloroacetate | I or IV | " | 0.75 g |
| 43 | 2-p-methoxyphenylthio ethylamine ditartrate | I or IV | " | 0.75 g |
| 44 | 2-tolylthio ethylamine hydrobromide | I or IV | " | 1.0 g |
| 45 | 2-(1-biphenyl thio) ethylamine hydrochloride | I or IV | " | 1.0 g |
| 46 | N—(2-pentachlorophenylthio ethyl) acetamide | I or IV | " | 1.5 g |
| 47 | 2-benzylthio ethylamine malate | I or IV | " | 1.5 g |
| 48 | 2-benzylthio ethylamine nicotinate | I or IV | " | 1.5 g |
| 49 | 2-benzylthio 2-methyl propylamine hydrochloride | I | " | 2.0 g |
| 50 | 2-benzylthio propylamine lactate | I | " | 2.0 g |
| 51 | N—(2-benzylthio ethyl)nicotinamide hydrochloride | VI | " | 2.5 g |
| 52 | N—(2-benzylthio ethyl) 10-undecene amide | VII or IV | " | 3.0 g |
| 53 | N—(2-benzylthio ethyl) hexadecanamide | VII or IV | " | 3.0 g |
| 54 | S—($\beta$-aminoethyl) mercaptobutyric acid | I | " | 4.0 g |
| 55 | N—(2-benzylthio ethyl)formamide | VII | " | 4.0 g |
| 56 | N—(2-benzylthio ethyl)phenylacetamide | VII or IV | " | 5.0 g |
| 57 | N—[2-(2,6-dimethyl phenyl)ethyl] hexanamide | VII or IV | " | 5.0 g |
| 58 | 2-(o-aminophenylthio) ethylamine succinate | I or IV | Milk as in Ex. 67–70 | 0.5 g |
| 59 | N—(2-benzylthio ethyl) glutamine | VII | " | 0.5 g |
| 60 | (S—$\gamma$-amino propyl) mercapto acetic acid | I | " | 0.5 g |
| 61 | S(2-p-methoxybenzamido ethyl) mercapto acetic acid | I | " | 0.5 g |
| 62 | 2-(2-naphtyl methylthio) ethylamine hydrochloride | I or IV | " | 1.0 g |
| 63 | 2-(2-naphtyl methylthio) ethylamine disuccinate | I or IV | " | 1.0 g |
| 64 | 2-(2-thenyl thio) ethylamine hydrobromide | I or IV | " | 1.0 g |
| 65 | N—[2-(2-thenylthio) ethyl] acetamide | VII or IV | " | 1.5 g |
| 66 | 2-(o-chlorobenzylthio) ethylamine hydrochloride | I or IV | " | 1.5 g |
| 67 | 2-(p-chlorobenzylthio) ethylamine glycolate | I or IV | " | 2.0 g |
| 68 | 2-(o-fluorobenzylthio) ethylamine hydrochloride | I or IV | " | 2.0 g |
| 69 | 2-furfurylthio ethylamine hydrochloride | I or IV | " | 2.5 g |
| 70 | 2-tetrahydrofurfurylthio ethylamine p-amino-benzoate | I or IV | " | 2.5 g |
| 71 | 2-$\beta$-phenylethylthio ethylamine glutamate | I or II | " | 3.0 g |
| 72 | 2-triphenyl methylthio ethylamine hydrochloride hemihydrate | I or III | " | 3.0 g |
| 73 | 2-(2-pyridyl ethylthio)ethylamine hydrochloride | I or II | " | 3.0 g |
| 74 | 2-(2-p-toluene sulfonamide ethylthio) | VII | " | 3.5 g |

TABLE II-continued

| No. | Active Compound | Method of Preparation | Form of Composition | Amount in Composition |
|-----|-----------------|----------------------|---------------------|----------------------|
| | pyridine N—oxide | | | |
| 75 | 2-β-aminoethylthiomethyl pyridine N—oxide dihydrochloride | I | " | 4.0 g |
| 76 | 2-β-aminoethylthio pyridine N—oxide hydrochloride | I | " | 4.0 g |
| 77 | 2,4-dichloro 2-benzylthio ethylamine aspartate | I or IV | " | 4.5 g |
| 78 | N—[2-(3,4-dichloro benzylthio)ethyl] butyramide | VII or IV | " | 4.5 g |
| 79 | N—[2-(2,6-dichloro benzylthio)ethyl] dodecanamide | VII or IV | " | 4.5 g |
| 80 | N—[2-(3,5-dichloro benzylthio)ethyl] trifluoroacetamide | VII or IV | " | 5.0 g |
| 81 | 2-o-methoxy benzylthio ethylamine hydrochloride | I or IV | " | 5.0 g |
| 82 | 2-p-ethoxybenzylthio ethylamine hydrochloride | I or IV | Foaming gel as in Ex. 73 | 1.0 g |
| 83 | N—[2-m-fluorobenzylthio ethyl] chloracetamide | VII | " | 1.0 g |
| 84 | 2-p-bromobenzylthio ethylamine succinate | I or IV | " | 1.0 g |
| 85 | 2-(3,4-dimethoxy benzylthio)ethylamine | I or IV | " | 2.0 g |
| 86 | 2-(3,4-methylenedioxy benzylthio)ethylamine hydrochloride | I or IV | " | 2.0 g |
| 87 | 2-(2,4-dichloro cetylthio)ethylamine | | Foam as in Ex. 74 | 1.0 g |
| 88 | 2-(3,4,5-trimethoxy benzylthio)ethylamine hydrocinnamate | I or IV | " | 1.0 g |
| 89 | 2-p-methoxy benzylthio ethylamine salicylate | I or IV | " | 2.0 g |
| 90 | 2-o-methylbenzylthio ethylamine phenyl-acetate | I or IV | " | 2.0 g |
| 91 | N—[2-p-dimethylaminobenzylthio ethyl] methane-sulfonamide | VII or IV | " | 3.0 g |
| 92 | 2-p-phenoxybenzylthio ethylamine hydrochloride | I or IV | Shampoo as in Ex. 80–89 | 1.0 g |
| 93 | 2-β-aminoethylthio pyridine hydrochloride | I or IV | " | 1.0 g |
| 94 | 2-benzylthio ethylamine citrate | I or IV | Shampoo as in Ex. 80–87 | 1.0 g |
| 95 | N—[2-benzylthio ethyl] 2,4-dihydroxy 3,3-dimethyl butyramide | VII | " | 1.5 g |
| 96 | N—[2-(2-pyridyl thio)ethyl] propionamide | VII or IV | " | 1.5 g |
| 97 | 2-(2-pyridyl methylthio)ethylamine dihydrochloride | I | " | 2.0 g |
| 98 | 2-benzylthio ethylamine pantothenate | I or IV | " | 2.0 g |
| 99 | S—(β-acetamidoethyl)mercaptoacetate of β-morpholinoethyl | V or IV | " | 2.0 g |
| 100 | S(β-phenylacetamidoethyl)mercaptoacetate of N'—methyl 2-piperazino ethyl | V or IV | " | 3.0 g |
| 101 | S—(β-ureidoethyl)mercaptoacetate of β-pyrrolidino-ethyl | V | " | 3.0 g |
| 102 | S—(β-trifluoroacetamidoethyl)-β-mercaptopropionate of β-dimethylaminoethyl | V | " | 3.5 g |
| 103 | 2-p-nitrobenzylthio ethylamine crotonate | I or IV | " | 4.0 g |
| 104 | 2-β-morpholinocarbonyl ethylthio ethylamine hydrochloride | I or II | " | 4.0 g |
| 105 | N,N—di-(hydroxyethyl)S—(β-benzamide-ethyl)mercapto-acetamide | I or IV | Permanent Wave as composition as in Ex. 93–95 | 0.5 g |
| 106 | N(2-N'—methyl piperazino carbonylthio) ethyl acetamide | I | Permanent Wave as composition as in Ex. 93–95 | 0.5 g |
| 107 | 2-(1-naphthyl thio)ethylamino hydrochloride | I or IV | Permanent Wave as composition as in Ex. 93–95 | 1.0 g |
| 108 | N—(3-β-ureidoethylthio propyl) succinamic acid | VII | Permanent Wave as composition as in Ex. 93–95 | 1.0 g |
| 109 | 3-allythio propylamine | I | Permanent Wave as composition as in Ex. 93–95 | 1.0 g |
| 110 | 3-(2,2'-dimethoxy ethylthio)propylamine | I | Permanent Wave as composition as in Ex. 93–95 | 2.0 g |
| 111 | 3-(2-2'-dimethoxy ethylthio)propylamine sulfate | VII or IV | Permanent Wave as composition as in Ex. 93–95 | 2.0 g |
| 112 | N—(2-benylthio ethyl)acetamide | VII or IV | Grooming lotion as in Ex. 39–42. | 0.1 g |
| 113 | N—(2-benzylthio ethyl)propionamide | VII or IV | " | 0.1 g |
| 114 | N—(2-benzylthio ethyl)butyramide | VII or IV | " | 0.1 g |
| 115 | N—(2-benzylthio ethyl)methanesulfonamide | VII or IV | " | 0.2 g |
| 116 | N—(2-benzylthio ethyl)ethanesulfonamide | VII or IV | " | 0.2 g |
| 117 | N—(2-benzylthio ethyl)propanesulfonamide | VII or IV | " | 0.2 g |

TABLE II-continued

| No. | Active Compound | Method of Preparation | Form of Composition | Amount in Composition |
|---|---|---|---|---|
| 118 | N—(2-benzylthio ethyl)butanesulfonamide | VII or IV | " | 0.5 g |
| 119 | S—(2-p acetamido benzene sulfonamido ethyl) mercapto acetic acid | I or IV | " | 0.5 g |
| 120 | S—(2-p-acetamidobenzamide ethyl) mercapto acetic | I or IV | " | 0.75 g |
| 121 | N—(2-thenylthio ethyl) amine hydrochloride | I or IV | " | 0.75 g |
| 122 | S—(2-p-butoxybenzamido ethyl)mercapto acetic acid | I or IV | " | 1.0 g |
| 123 | 2-methoxycarbonyl methylthio ethylamine hydrochloride | V | " | 1.0 g |
| 124 | 2-propoxycarbonylmethylthio ethylamine | V | " | 2.0 g |
| 125 | 2-butoxycarbonylmethylthio ethylamine | V | Dermal Milk as in Ex. 43–44 | 0.1 |
| 126 | 2-benzylthio ethylammonium diacid phosphate | I or IV | " | 0.1 g |
| 127 | N—(2-methylthio ethyl)nicotinamide | VII or IV | " | 0.2 g |
| 128 | N—(2-methylthio ethyl)benzamide | VII or IV | " | 0.2 g |
| 129 | N—(2-methylthio ethyl)p-methoxybenzamide | " | " | 0.5 g |
| 130 | N—(2-methylthio ethyl)p-butoxybenzamide | " | " | 0.5 g |
| 131 | N—(2-methylthio ethyl)butyramide | " | " | 1.0 g |
| 132 | N—(2-methylthio ethyl)propionamide | VII or IV | " | 1.0 g |
| 133 | N—(2-methylthio ethyl)acetamide | VII or IV | " | 1.0 g |
| 134 | N—(2-methylthio ethyl)butanesulfonamide | " | " | 1.0 g |
| 135 | N—(2-octylthio ethyl)methanesulfonamide | " | " | 1.0 g |
| 136 | 2-methylthio ethylammonium undecylenate | I or IV | " | 2.0 g |
| 137 | N—(methylthio ethyl)p-acetamido benzamide | VII or IV | " | 2.0 g |
| 138 | N—(2-benzylthiopropyl)nicotinamide | VI | " | 5.0 g |
| 139 | S—(2-p-methoxy benzamido ethyl)mercapto acetic acid | I or IV | " | 5.0 g |
| 140 | N—(2-methylthio ethyl)p-acetamido benzene sulfonamide | VII or IV | lotion as in Ex. 45–54 | 0.1 g |
| 141 | 2-tritylthio propylamine | I | " | 0.1 g |
| 142 | 2-methylthio ethylammonium dihydro cinnamate | I or IV | " | 0.1 g |
| 143 | 2-benzylthio ethylammonium p-toluene sulfonate | I or IV | " | 2.0 g |
| 144 | 2-benzylthio ethyl ammonium salicylate | " | " | 2.0 g |
| 145 | 2-benzylthio ethyl ammonium ditartrate | " | " | 2.5 g |
| 146 | N—(2-benzylthio ethyl)nicotinamide | VII | " | 4.0 g |
| 147 | N—(2-tetradecylthioethyl)picolinamide | VII | " | 4.0 g |
| 148 | N—N'—(2,2'-thio diethyl)bis(2-pyridyl mercapto-acetamide) | VII | cream or milk as in Ex. 60–66 | 0.5 g |
| 149 | 2-(benzylmethanesulfonylamido)3-dodecylthio propionic acid | VII | " | 0.5 g |
| 150 | N—(o-fluoro 2-benzylthioethyl)2-p-chlorophenoxy 2-methy propionamide | VII | " | 0.75 g |
| 151 | 2-benzylthio ethylammonium orotate | I or IV | " | 0.75 g |
| 152 | 2-(p-chlorophenoxy)2-methyl propionate of 2-benylthio ethyl ammonium | I or IV | Milk as in Ex. 67–70 | 0.5 g |
| 153 | 2-p-chlorophenylthio ethylammonium N—oxyde picolinate | I or IV | " | 0.5 g |
| 154 | S—(2-pyridyl N—oxyde)mercaptoacetate of 2-benzylthio ethylammonium | I or IV | " | 0.5 g |

All the preceding compounds except compounds 18, 26, 28 and 87 are new; the following compounds are known compounds:

| No. | Active Compound | Method of Preparation | Form of Composition | Amount in Composition |
|---|---|---|---|---|
| 155 | 2-dodecylthio ethylamine hydrochloride | I or IV | Foam gel as in Ex. 73 | 1.0 g |
| 156 | S—β-ureidoethyl thiocarbamate | VIII | " | 1.0 g |
| 157 | 5-β-aminoethylthio pentanoic acid | II | " | 2.0 g |
| 158 | S—β-aminoethyl mercapto acetic acid | I | " | 2.0 g |
| 159 | (3-S—β-aminoethyl)mercapto propionic acid | II | " | 2.0 g |
| 160 | 2-diphenylmethylthio ethylamine hydrochloride | I or III | " | 2.0 g |
| 161 | N—(2-benzylthio ethyl) 6,8-dihydroxy 7,7-dimethyl 5-oxo 4-aza octanamide | VII | Foam as in Ex. 74 | 1.0 g |
| 162 | N—formyl S—methyl penicillamine | I | " | 1.0 g |
| 163 | The hydrochloride of S—β-aminoethyl mercapto acetic acid | I | " | 3.0 g |
| 164 | 2-t-butylthio ethylamine hydrochloride | III | Shampoo as in Ex. 80–89 | 1.0 g |
| 165 | 2,2'-thio diethylamine dihydrochloride | I or IV | " | 1.0 g |
| 166 | 3-(2-aminoethylthio)alanine hydrochloride | I or IV | " | 1.0 g |
| 167 | 2-methylthio ethylammonium phenylacetate | I or IV | Permanent wave composition as in Ex. 93–95 | 0.5 g |
| 168 | 2-benzylthio ethylamine hydrochloride | I | Permanent wave composition as in Ex. 93–95 | 1.5 g |
| 169 | 2-benzylthio ethylamine hydrobromide | I | Permanent wave composition as in Ex. 93–95 | 2.0 g |

What is claimed:

1. 5-ureido-3-thia hexanedioic acid.

* * * * *

UNITED STATES PATENT AND TRADEMARK OFFICE
CERTIFICATE OF CORRECTION

PATENT NO. : 4,396,520

DATED : August 2, 1983

INVENTOR(S) : Nicholas S. Payne et al

It is certified that error appears in the above-identified patent and that said Letters Patent is hereby corrected as shown below:

Column 6, line 30, Claim 14, "benzoate" should be -- benzene --.

Signed and Sealed this

Twentieth Day of November 1984

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,394,520
DATED : July 19, 1983
INVENTOR(S) : Gregoire KALOPISSIS

It is certified that error appears in the above-identified patent and that said Letters Patent is hereby corrected as shown below:

Title page:

[60] Related U.S. Application Data

"Ser. No. 714,004" should read --Ser. No. 714,000--.

[30] Foreign Application Priority Data

"April 19, 1969" should read --April 19, 1968--.

Signed and Sealed this

Nineteenth Day of March 1985

[SEAL]

Attest:

DONALD J. QUIGG

Attesting Officer    Acting Commissioner of Patents and Trademarks